United States Patent [19]

Kinra

[11] Patent Number: 5,305,239
[45] Date of Patent: Apr. 19, 1994

[54] ULTRASONIC NON-DESTRUCTIVE EVALUATION OF THIN SPECIMENS

[75] Inventor: Vikram K. Kinra, College Station, Tex.

[73] Assignee: The Texas A&M University System, College Station, Tex.

[21] Appl. No.: 416,889

[22] Filed: Oct. 4, 1989

[51] Int. Cl.[5] .............................................. G06F 15/20
[52] U.S. Cl. ...................................... 364/507; 73/602; 364/563
[58] Field of Search .................. 73/602; 364/507, 563; 367/13

[56] References Cited

U.S. PATENT DOCUMENTS

| | | | |
|---|---|---|---|
| 4,274,288 | 6/1981 | Tittmann et al. | 73/602 |
| 4,307,614 | 12/1981 | Tittman et al. | 73/629 |
| 4,452,082 | 6/1984 | Miwa | 73/602 X |
| 4,512,194 | 4/1985 | Beuter | 73/602 X |
| 4,545,250 | 10/1985 | Miwa | 73/602 |
| 4,555,767 | 11/1985 | Case et al. | 364/563 |
| 4,571,999 | 2/1986 | Arita et al. | 73/602 X |
| 4,574,635 | 3/1986 | 't Hoen | 73/602 X |
| 4,924,449 | 5/1990 | Guigné | 367/92 X |
| 5,035,144 | 7/1991 | Aussel | 73/602 |

*Primary Examiner*—Edward R. Cosimano
*Attorney, Agent, or Firm*—Baker & Botts, L.L.P.

[57] ABSTRACT

In the field of non-destructive evaluation of materials, conventional ultrasonic measurement techniques are limited to materials having a thickness which is relatively large compared to the wavelength of the ultrasonic signal used. The present technique enables the accurate ultrasonic non-destructive measurement of materials which are relatively small compared to the wavelength of the ultrasonic signal used. Ultrasonic signals received from a thin material are processed in the frequency-domain either directly or by use of a Fast Fourier Transform. Specifically, the frequency response of the ultrasonic transducers used in the measurement is removed from the frequency response of the signal received when measuring the material. This yields a frequency response which is indicative of the material alone. Then, the measured frequency response of the material is evaluated to determine unknown parameters of the material. For instance, the phase of the measured signal is determined over a predetermined frequency range (usually the bandwidth of the transducers), and the phase is used to determine the speed of ultrasonic waves travelling in the material for frequencies within the predetermined range. Likewise, the magnitude of the measured signal is determined over the predetermined frequency range, and the magnitude is used to determine the attenuation of ultrasonic waves travelling in the material for frequencies within the predetermined range.

21 Claims, 8 Drawing Sheets

ULTRASONIC NON-DESTRUCTIVE EVALUATION OF THIN SPECIMENS

This invention was made with Government support under contract AFOSR-84-0066 awarded by the Air Force Office Of Scientific Research. The Government has certain rights in this invention.

BACKGROUND OF THE INVENTION

1. Technical Field

This invention relates generally to the ultrasonic-nondestructive evaluation of materials, and more particularly to the ultrasonic-nondestructive evaluation of materials having a thickness of one millimeter or less.

2. Description of the Related Art

The ability of sound to propagate through a solid material, without affecting the material in any way, makes it an ideal nondestructive testing tool. By way of example, for many, many years the integrity of earthen pots has been tested by banging the pots with a stone and observing the changes in the tone of the sound produced. Through the use of modern electronics, this primitive testing technique has been modified and refined. The stone has been replaced with a piezoelelectric transmitting transducer, and the ear has been replaced with a piezoelectric receiving transducer.

The wavelength of a signal imparted into a material is inversely proportional to the frequency of the signal, so at higher frequencies the wavelength is very small in comparison to the overall dimensions of the material being tested. When the wavelength is very small in comparison to the size of the material, the size of the material does not affect the sound waves as they travel through the material. Therefore, signals in the ultrasonic frequency range (greater than 20 kHZ) are used to test various parameters of a wide variety of materials.

In non-dispersive isotropic medium, such as air, the speed of sound can be accurately measured using the well known "time of flight" method. Using the time of flight method, sound waves are injected into the air at one point and received at a distant point. The time that it takes the sound to travel from the first point to the distant point is recorded and the speed of sound calculated. In a non-dispersive isotropic medium, the phase velocity and the group velocity are identical. However, if the material is dispersive, then the time of flight method does not deliver accurate results. In order for the wavespeed in this type of material specimen to be measured, a "tone burst" method is used. Using the tone burst method, a burst of monotonic sound, typically of about ten cycles in duration, is injected into the specimen. FIG. 1 illustrates a typical measurement arrangement where a material specimen 100 is placed within an elastic medium 102, such as water, and ultrasonic energy, in this case a tone burst, is injected into the specimen along ray 1. The front face of the specimen is placed at a pre-selected coordinate, x=a, and, therefore, the back face of the specimen is located at coordinate x=b. The thickness h of the specimen 100 is defined as h=b−a.

When the incident wave (ray 1) strikes the material specimen 100 of thickness h, it is partially reflected as shown by ray 2, and partially transmitted as shown by ray 3. The wave illustrated by ray 3 is partially reflected by the back surface of the specimen 100 as shown by ray 5, and partially transmitted as shown by ray 4. This process continues indefinitely as shown by the successive rays 6–20. The time interval t between the first two reflected waves (rays 2 and 6) or between the first two transmitted waves (rays 4 and 8) is measured, and the wavespeed calculated using the equation:

$$c = 2h/t, \quad (1)$$

where c is the wavespeed, h is the thickness of the material specimen and t is the measured time. Attenuation is measured by fitting an exponential curve through the amplitudes of wave 2, 6, 10, etc.

While this method works well when the material specimen is sufficiently thick so that the signals are separable in the time-domain, as shown in FIGS. 2a and 2b, it cannot be used for thin specimens where the signal are not separable in the time-domain, as shown in FIGS. 2c–2e. In FIG. 2a, the first pulse 30 is the measured signal corresponding to the first reflected wave (ray 2), the pulse 32 is the measured signal corresponding to the second reflected wave (ray 6), the pulse 34 is the measured signal corresponding to the third reflected wave (ray 10), the pulse 36 is the measured signal corresponding to the fourth reflected wave (ray 14), and the pulse 38 is the measured signal corresponding to the fifth reflected wave (ray 18). Clearly, a starting point for each of these pulses can be chosen so that the distance between selected pulses may be measured.

However, since the signals are of a finite duration, when the material specimen is thin, the second reflected wave (ray 6) arrives before the first reflected wave (ray 2) has died out, and, similarly, the third reflected wave (ray 10) arrives before the second reflected wave (ray 6) has died out, and so on. Hence, a continuous arrival of signals is obtained as shown in FIGS. 2c–e. The measured signals from the reflected waves or from the transmitted waves cannot be separated so the time between the pulses cannot be measured. The time of flight method and the tone burst method cannot be used to accurately evaluate thin material specimens, but can only be applied to material specimens which have a thickness sufficient to allow the reflections from the faces of the specimen to be clearly separated in the time-domain. Therefore, the thickness of the material specimen should be large compared to the wavelength of the ultrasonic wave $\lambda$ injected into the specimen. For homogeneous materials, the thickness should be greater than approximately $3\lambda$, and for heterogeneous materials, the thickness of the material specimen should be greater than approximately $5\lambda$. Relatively thicker specimens may be needed for highly dispersive materials such as composites.

Since wavelength and frequency are inversely proportional, attempts to solve the problem of measuring wavespeed in thin specimens have concentrated on reducing the wavelength of the ultrasonic wave by increasing its frequency. This relationship is shown by the following equation:

$$c = f\lambda \quad (2)$$

where c=wavespeed, $f$=frequency and $\lambda$=wavelength. For example, using equations (1) and (2), to determine the wavespeed in a one millimeter thick aluminum plate, one would need to use a frequency of approximately 15 MHz since the wavespeed in aluminum is 6.38 mm/$\mu$s. Likewise, in order to determine the wavespeed in a specimen having a thickness of 0.1 millimeters, one would need to use a frequency of 150 MHz.

Practically, this means that transducers capable of emitting acoustical energy at 15 MHz and at 150 MHz, respectively, must be used. This is a major disadvantage for the previous mentioned techniques, because 15 MHz transducers are extremely expensive, as compared to 1 MHz transducers for instance, and 150 MHz transducers are not readily available, commercially. Not only is the cost of the transducers prohibitive, but the cost of the associated electronics which are capable of accurately delivering and processing these extremely high frequencies increases exponentially with the frequency. Because of these problems, these ultrasonic non-destructive evaluation techniques are facing a wavelength barrier where the thickness of a material specimen to be evaluated must be several times greater than the wavelength.

In addition to the two techniques already mentioned, many other ultrasonic non-destructive evaluation techniques are known, however, they are all limited by of the thickness of the material specimen due to the use of the pulse separation as shown in FIGS. 2a and 2b. Refinements of the time-of-flight method include the pulse-superposition method and the pulse-echo method. Using these measurement techniques, the specimens have to be thick enough so that individual pulses can be distinguished in the time-domain. Moreover, if the specimen material is highly attenuating, then the pulse-superposition method cannot be used, and if the specimen material is dispersive, then the pulse-echo method gives unreliable results.

The "ultrasonic spectroscopy" method was developed for measuring wavespeed in thin composite laminates. The reflected pulse from the front face of the laminate and the reflected pulse from the rear face of the laminate are digitized and transformed into the frequency-domain by a Fast Fourier Transform. Interference between these two reflected pulses produces resonance dips in the amplitude of the transformed signals, and the spacing between these dips can be related to wavespeed. Using this technique, wavespeed can be measured in specimens of about 2 millimeters in thickness over a frequency range of 5 to 11 M Hz. The limitations of this method are: (a) it requires pulse separation; (b) it is not conducive to automation; (c) in materials having high attenuation, the resonance dips are not sharp, and, thus, the method is prone to errors; and (d) when the spacing between the resonance dips is large, the method yields very inaccurate results.

It should be remembered that wavespeed and attenuation of a material specimen can be used to determine many parameters of the material specimen. For instance, if the wavespeed in a particular type of material is known and if the time that it takes for the ultrasonic wave to pass through the material can be measured, then the thickness of the material can be determined, as shown by equation (1). If the thickness of the material specimen is known, then an elastic modulus of the material can be determined. For instance, if the wavespeed and the density of the material is known, then the stiffness of the material can be determined.

It is important to reiterate that ultrasonics were originally used to determine the integrity of a material or structure. The ultrasonics eliminate the effect of the size of the structure, and, therefore, any scattering of the ultrasonic wave is due to a flaw in the structure. Ultrasound has been used to detect cracks, holes, porosity and non-homogeneity in isotropic materials. Basically, an ultrasonic wave is launched into a specimen, and the sound is scattered from the defects and detected by a receiving transducer. The depth of a defect can be estimated by measuring the time of flight from the emitter to the receiver, and the extent of damage can be mapped by moving the transducer over the damage and observing the reflections. The reflections from other surfaces, such as the back surface of the specimen, can be gated out and reflections from the defect isolated.

It is well known that the wavespeed of sound in an elastic material is related to its stiffness, $E=c^2p$, where $E=$stiffness, $c=$the wavespeed, and $p=$density. The presence of defects, such as voids, cracks, particles, and delaminations, changes the effective stiffness of the material. When an acoustical wave has propagated through such a material, the change in stiffness is manifested as a change in the sound velocity as shown in the previous equation. Furthermore, the defects tend to scatter the sound waves, and, as a result, the defect population also produces attenuation of the wave as it passes through the material.

Various researchers have used ultrasonics for the non-destructive evaluation of the composites by relating the acoustic parameters of the composites to the damage or defects in the composite. The transmission of ultrasonic energy through a composite material in the direction of its thickness has been used for flaw detection in metals. If there are no cracks in the specimen, the waves pass through undisturbed. When the waves encounter cracks, however, the energy is scattered by the cracks, and, as a result, wave intensity is reduced.

Composites are finding an ever increasing use as structural material, especially in the aerospace and automotive industries. In the early stages of the development of composites, composites were used as secondary structural members such as control surface panels. As the reliability of composites increased and material with higher strength-to-weight ratios have been produced, composites are now being used as primary load bearing members. Therefore, information regarding the integrity of composites such as these is growing more useful and often vital.

The mechanical and thermal loading cycles that the structures have to undergo create damage in the composite structures. While a wide variety of nondestructive evaluation techniques which were originally developed for homogeneous materials have been used on composite materials with some success, the damage development in composites is quite different from the damage development in isotropic materials. In isotropic materials when the damage is initiated, it becomes the nucleating sight for further damage growth. Any further loading causes the stress concentration around the damage to produce greater damage. The growth mechanism and growth rates for isotropic homogeneous materials are fairly well understood, and hence, the main task for the nondestructive evaluation of such materials is to detect and record the damage as early as possible in its growth life. Once this information is available, reasonable prediction of the residual stiffness and of the remaining life of the component can be determined.

Conversely, in composite materials, and especially in continuous fiber composites, a very different phenomenon takes place. In composites, very strong fibers, such as graphite fibers, are embedded in a weaker matrix, such as epoxy. As a result, matrix cracking is usually the first mode of damage in composites because the matrix is not nearly as strong as the fibers. Fortunately, however, the fibers help contain the matrix cracks in two ways: (1) fibers inhibit the crack growth by acting as crack arresters; and (2) fibers, being much stronger than the matrix, are able to carry the extra load due to the load redistribution of stresses in the vicinity of the damage, and, thus, some amount of stress relieving takes place in the matrix. Therefore, once a composite has been damaged, further loading of the composite causes the next crack in the matrix to occur at a different location where the matrix stress has reached a critical value. As a result of this phenomenon, the entire composite structure develops micro-cracks without seriously endangering the overall integrity of the structure.

The immediate effect of this distributed damage is in the form of reduced stiffness and higher damping of the structure. Continued damage to the composite structure causes the response of the structure to change under load. For example, the reduced stiffness of the wing of an aircraft will cause extra deflection and possibly torsion, both of which may change the aerodynamic configuration of the wing. The evaluation of a composite structure after it has undergone a certain amount of loading and damage is useful in evaluating the performance of the structure. Therefore, the interest is not only the detection and location of a defect, but also the evaluation of the effects of continued microdamage on the mechanical response of a component. Almost all of the non-destructive evaluation techniques listed earlier can detect macrosize flaws, but cannot measure the changes in mechanical response of the materials caused by distributed damage.

Another area of interest is the testing of adhesive bond strength, particularly for in-situ applications. However, there does not exist any reliable method for the non-destructive evaluation of adhesive interfaces. This, again, is due to the fact that the wavelength of an ultrasonic wave is much larger than the bond-line thickness of an adhesive interface. Since the previously mentioned methods of ultrasonic non-destructive evaluation rely on the separation of successive pulses in the time-domain, these methods are not useful in the evaluation of thin adhesive bonds. Since adhesives are often used in critical structural applications, such as the adhesion of ceramic tiles to the United States space shuttles to protect them against the heat of re-entry, a method of non-destructive evaluation which will determine the integrity of the adhesive bonds is badly needed.

SUMMARY OF THE INVENTION

In accordance with one aspect of the present invention, there is provided a method for non-destructively evaluating a material wherein an ultrasonic wave having a frequency within a predetermined frequency range is transmitted into the material. The ultrasonic wave is received from material, either from reflection or transmission, and a frequency response of the material at frequencies within the predetermined frequency range is measured from the received ultrasonic wave. From the measured frequency response a frequency-dependent normalized wavenumber is determined.

The wavenumber is a complex mathematical quantity, i.e., it has a real portion and an imaginary portion, which contains information regarding the material being evaluated. For instance, the real portion is correlative to a speed of the ultrasonic wave within the material, where the speed is dependent upon the frequency of ultrasonic wave, and the imaginary portion is correlative to an amount of attenuation of the ultrasonic wave produced by the material, where the attenuation is dependent upon the frequency of the ultrasonic wave.

Preferably, the magnitude of the measured frequency response is determined within the predetermined frequency range, because the magnitude is correlative to the attenuation of the material within the predetermined frequency range. Also, the phase of the measured frequency response is determined within the predetermined frequency range, because the phase is correlative to the speed of ultrasonic waves in the material within the predetermined frequency range.

If the attenuation and the wavespeed of the material is known, then the thickness of the material can be determined.

DESCRIPTION OF THE PREFERRED EMBODIMENTS

Time-Domain Technique

Figure 1:
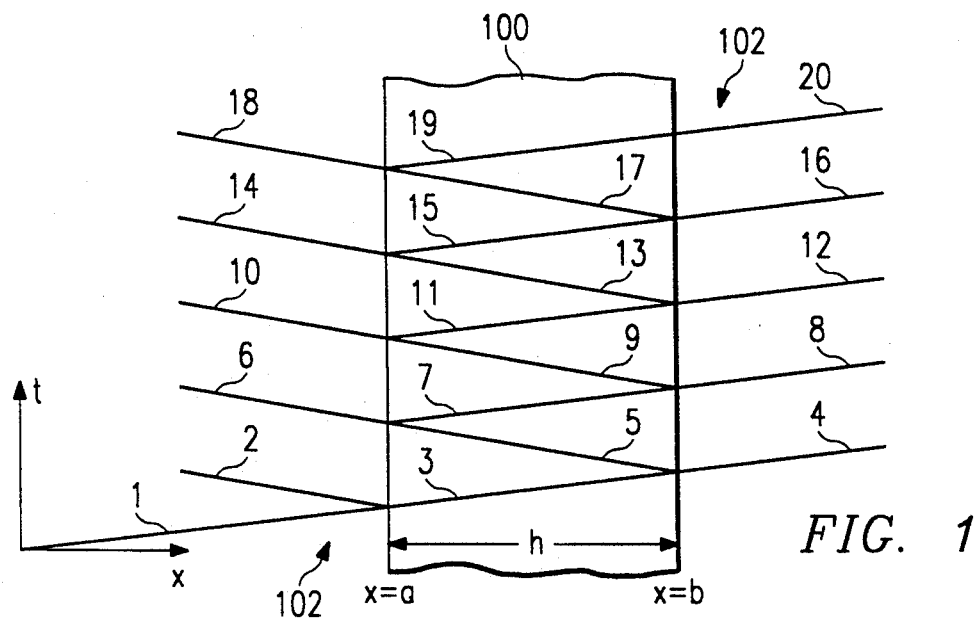
FIG. 1 illustrates reflections and transmissions of a wave as a function of time.

Turning now to the drawings and referring initially to FIG. 1, a material specimen 100, preferably an elastic plate, is shown to be immersed in an elastic fluid 102, such as water. The rays 1-20 indicate the space-time location of a wave front which occupied the position $x=0$ at time $t=0$. Preferably, ray 1 represents a plane-fronted finite-duration pulse normally incident on the plate 100. The incident displacement wave (ray 1) produces an infinite series of reflected and transmitted displacement waves as it passes through the specimen 100 and reflects off of the surfaces of the specimen. The displacement in the incident wave (ray 1) is given by:

$$u^{inc} = f_o(wt - k_o x) \qquad (3)$$

where $f_o(s)=0$ for values of $s<0$, $w$ is the circular frequency, and $k_o$ is the wavenumber of a monochromatic harmonic wave in the elastic fluid 102. The displacement field along the various reflected waves, rays 2, 6 and 10 respectively, are written as $$u_2 = R_{12} f_0(s-s_2); \quad s_2 = 2k_0a, \qquad (4)$$

$$u_6 = T_{12}R_{21}T_{21}f_0(s-s_6); s_4 = 2k_0a + 2kh, \qquad (5)$$

$$u_{10} = T_{12}R_{21}T_{21}f_0(s-s_{10}); s_{10} = 2k_0a + 4kh, \qquad (6)$$

where $h=b-a$ is the plate thickness, $R_{ij}$ is the reflection coefficient in medium i from medium j, $T_{ij}$ is the transmission coefficient for a wave incident in medium i and transmitted into medium j, and $k=w/c$ where c is the wavespeed of the acoustical wave in the plate 100. Of more importance, however, the entire reflected field may be treated as a summation of all of the reflected waves from $u_2$ to $u_\infty$. Therefore, the displacement field for the entire reflected field is given by:

$$u^r = R_{12}f_0(s-s_2) + T_{12}R_{21}T_{21} \sum_{m=1}^{\infty} R_{21}^{m-1} f_0(s-s_m), \qquad (7)$$

where $s_m = 2k_0a + m2kh$.

In an analogous manner, the expressions for the transmitted pulses, where $s = wt - k_o x$ (thus indicating that the waves are traveling in the positive x direction), are given by:

$$u_4 = T_{12}T_{21}f_o(s-s_4); \quad s_4 h(k-k_o), \qquad (8)$$

$$u_8 = T_{12}R_{21}T_{21} f_o(s-s_8); \quad s_8 = h(3k-k_o), \qquad (9)$$

$$u_{12} = T_{12}R_{21}T_{21}f_o(s-s_{12}); \quad s_{12} = h(5k-k_o) \qquad (10)$$

Likewise, the total transmitted field is written as:

$$u^t = T_{12}T_{21} \sum_{m=1}^{\infty} R_{21}^{2m} f_0(s-s_m); \quad s = h[(2m+1)k-k_o] \qquad (11)$$

In equations (7) and (11), m is the number of complete round trips taken by the wave across the plate 100 having a thickness h.

Having given a mathematical representation for each of the reflected and transmitted waves, and for the total reflected field and the total transmitted field, it will be shown how the signals are processed to evaluate a variety of material specimens. First, the individual waves will by processed to evaluate a relatively thick specimen. As discussed previously in regard to the related art, a thick specimen is one having a thickness h greater than about five wavelengths of the ultrasonic wave in the specimen. Therefore, if the specimen is relatively thick, the various pulses in FIG. 1 can be clearly separated from each other in the time-domain. Subsequently, the received waves corresponding to the total reflected or transmitted field will be processed to evaluate a thin specimen, since the individual pulses cannot be separated.

Briefly, the received signals, whether representative of an individual pulse or of the total reflected or transmitted field, are converted into the frequency-domain by a Fourier Transform. For instance, a Fourier Transform for a function $f(t)$ is defined as:

$$F^*(w) = \frac{1}{\sqrt{2\pi}} \int_{-\infty}^{\infty} f(t)e^{-iwt} dt, \quad -\infty < w < \infty \qquad (12)$$

with the associated inverse transform being given by:

$$f(t) = \frac{1}{\sqrt{2\pi}} \int_{-\infty}^{\infty} F^*(w)e^{-iwt} dw \qquad (13)$$

A signal from the specimen, G*(w), is processed with a reference signal, F*(w), to yield information about the tested specimen, as will be discussed hereinafter.

Figure 3:
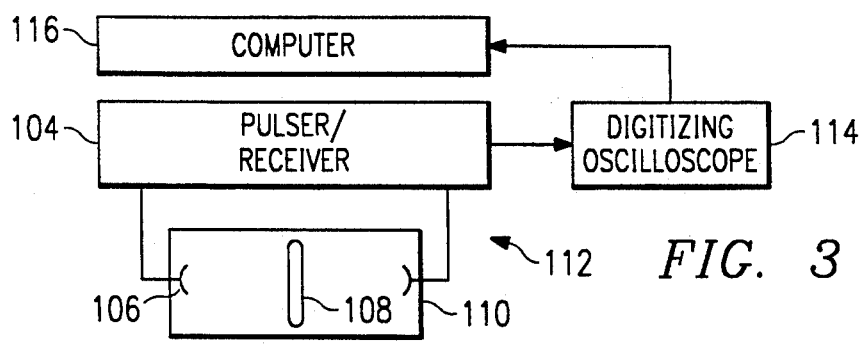
FIG. 3 is a block diagram of a testing apparatus for use in accordance with the present invention.

FIG. 3 illustrates a preferred apparatus for evaluating thick or thin specimens. A pulser/receiver 104 delivers an initiating electrical signal to a transducer 106 which converts the electrical signal into an acoustic ultrasonic pulse. Simultaneously, the pulser/receiver 104 delivers a signal which triggers a digitizing oscilloscope 114. The ultrasonic pulse is received by a specimen 108 which is immersed in an elastic fluid 110, such as water. This initiating pulse corresponds to the incident wave (ray 1) in FIG. 1, and is defined by equation (3). The pulse is variously reflected and transmitted by the specimen 108, and these reflections and transmissions are received by the transducer 106 and a transducer 112, respectively. Preferably, piezoelectric transducers are used. As the pulser/receiver 104 receives the reflected and transmitted signals from the transducers 106, 112, respectively, the respective signals are amplified by the pulser/receiver 104 and delivered to the digitizing oscilloscope 114. The oscilloscope 14, having been triggered to receive the signals, digitizes the received signals by sampling them at a sufficiently high rate to prevent aliasing. It has been found that for a short-duration pulse of about 100 nanoseconds, a sampling rate of 50 to 100 MHz produces very good results. A built in signal processor of the oscilloscope 114 performs a Fast Fourier Transform (FFT) on the received signals, and then delivers the data to a computer 166 for further processing.

1. Analysis of a Thick Specimen

Figure 2A:
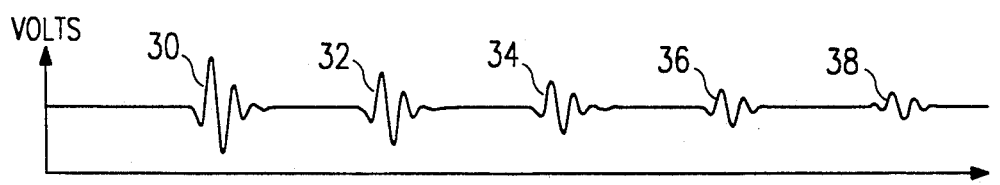
FIGS. 2a-e illustrate received reflected or transmitted pulses in the time-domain for a specimens of gradually decreasing thicknesses.
Figure 2B:
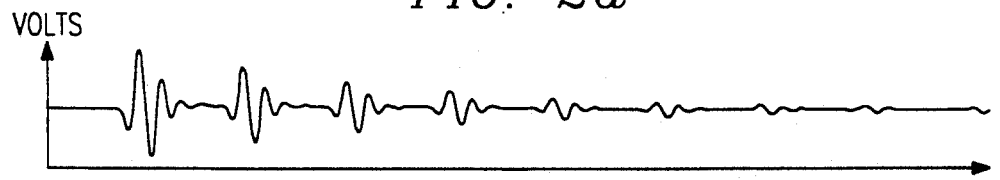
Figure 2C:
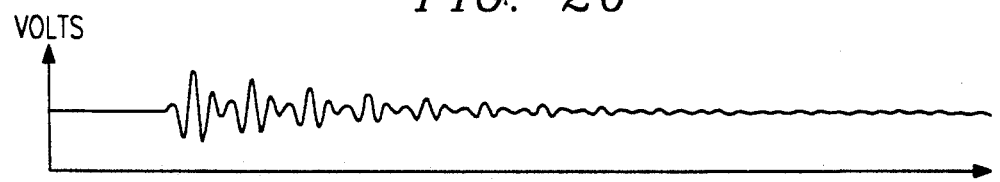
Figure 2D:
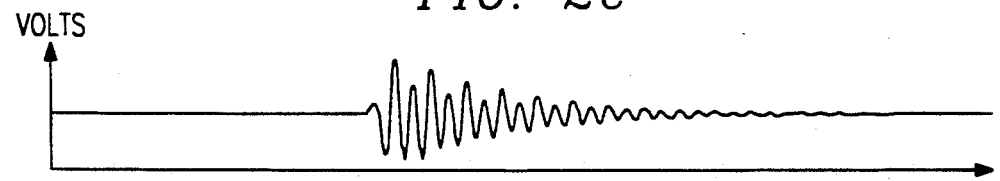
Figure 2E:
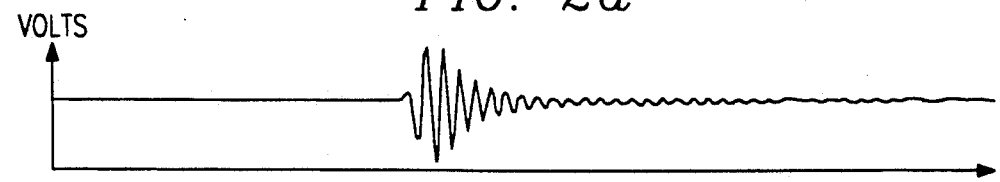

A specimen is defined s "thick" if the individual reflected or transmitted pulses can be separated in the time-domain, and a specimen is defined as "thin" if the individual reflected or transmitted pulses cannot be separated in the time-domain. This is shown graphically in FIGS. 2a-2e, where the thickness of a specimen of aluminum is gradually decreased from 2.807 millimeters to 0.258 millimeters. The aluminum specimen is excited by a 10 MHz ultrasonic wave. As shown in FIGS. 2a and 2b, the pulses 30-38 are easily distinguishable in the time-domain, thus indicating that the aluminum specimen is thick in comparison to the wavelength of the 10 MHz wave. However, as the thickness of the aluminum specimen decreases, as shown in FIGS. 2d-2e, a previous pulse does not die out before a subsequent pulse arrives. Therefore, the individual pulses can no longer be distinguished from one another, and the spacing between consecutive pulses cannot be measured. Hence, measurement techniques which rely on pulse separation are rendered ineffective as the thickness of the specimen decreases.

A. Reflection Method

In reference to FIG. 3, a thick specimen 108 is placed in the elastic fluid 110 between the transducers 106 and 112. The pulser/receiver 104 delivers a pulse to the transducer 106 to initiate the operation of the apparatus, as described above. First, only selected reflected waves will be used to evaluate the specimen 108, so the transducer 106, after delivering the incident pulse, becomes a receiving transducer. Therefore, $f(t)$ is the signal corresponding to the first reflected wave (ray 2) and g(t) is the signal corresponding to the first two reflected waves (rays 2 and 6), so:

$$f(t) = R_{12}f_0(wt - 2k_0a) \tag{14}$$

and $$g(t) = T_{12}R_{21}T_{21}f_0(wt - 2k_0a - 2kh) + f(t). \tag{15}$$

Generally speaking, the function f(t) is used as a reference signal which is indicative of the response of the transducers, and the function g(t) is the specimen signal which is indicative of the response of the specimen to ultrasonic waves. In the case of a thick specimen, the measurements of f(t) and g(t) are taken by isolating the first reflected pulse (ray 2) and the first and second pulses (rays 2 and 6), respectively. This type of isolation is referred to as "gating out" the successive pulses.

The Fourier Transforms of $f(t)$, g(t) and $f_0(t)$ are determined to transform the signals from the time-domain to the frequency-domain for further processing, and are defined by the equations set forth below.

$$F^*(w) = R_{12}e^{-i2k_0a}F^*_0(w) \tag{16}$$

$$G^*(w) = R_{12}F^*_0(w)e^{-i2k_0a}[1 - T_{12}T_{21}e^{-i2kh}] \tag{17}$$

Figure 4:
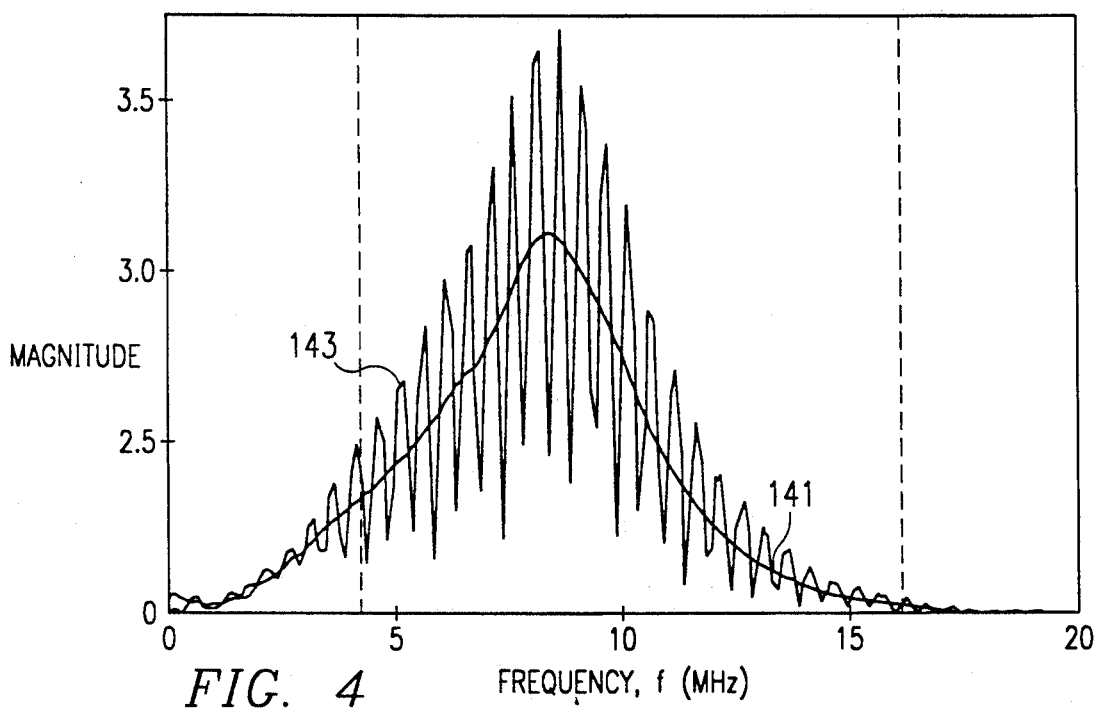
FIG. 4 illustrates a frequency response of a received signal.

Using equations (16) and (17), the absolute value of F*(w) vs. w and the absolute value of G*(w) vs. w are plotted, as shown in FIG. 4 as curves 141 and 143, respectively. Notice that the magnitude of G*(w) generally follows the frequency response curve 141 of the transducers, and is characterized by a series of resonance peaks whose spacing is given by:

$$\Delta(2hw/c) = 2\pi, \tag{18}$$

which can be rewritten as:

$$c = 2h\Delta f, \text{ since } w = 2\pi f. \tag{19}$$

Therefore, $\Delta f$ is the spacing between the peaks on the frequency axis. By measuring the spacing between the peaks, $\Delta f$ is determined and the wave velocity c is calculated using equation (19). However, this method is not conducive to automation in that it requires human judgement to measure the spacing between the peaks.

Figure 5:
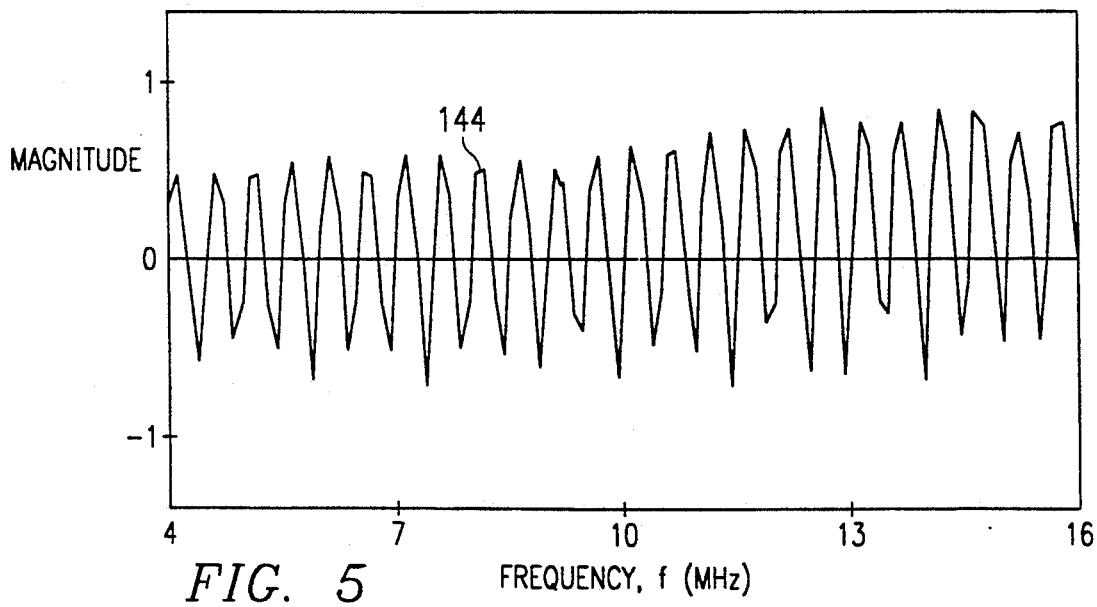
FIG. 5 illustrates a frequency response of a deconvolved signal.

To provide a technique which is conducive to automation, i.e., computer analysis, G*(w) and F*(w) are deconvolved, as shown in FIG. 5. This is equivalent to the simple operation of division in the frequency-domain. Accordingly, the transfer function, H*(w), is defined by:

$$H^*(w) = \frac{G^*(w)}{F^*(w)} = 1 - T_{12}T_{21}e^{-i2kh} \tag{20}$$

Using this deconvolution process, the frequency response of the transducers, F*(w), is removed from G*(w) shown in FIG. 4, and the resulting oscillation is due to the constructive and destructive interference between the first reflected wave (ray 2, reflected off of the front surface of the specimen) and the second reflected wave (ray 6, reflected off of the back surface of the specimen), so that curve 144 of FIG. 5 illustrates only the frequency response of the specimen. Now, instead of measuring the spacing between the peaks, the spacing between zero crossing points can be easily and precisely measured to obtain $\Delta f$. Using equation (19), if the wavespeed c through the material of specimen 108 is known, then the thickness h of the specimen 108 can be determined.

However, it is observed that as the thickness h decreases, $\Delta f$ increases, and fewer resonance peaks result. Since the peaks in FIG. 4 and the zero crossings in FIG. 5 are fewer and farther apart, the precision of this technique decreases as the thickness h decreases. Moreover, as $\Delta f$ becomes larger than the bandwidth of the transducers (shown by the dashed lines in FIG. 4), two peaks will not appear on curve 143 in FIG. 4 nor on curve 144 in FIG. 5.

To appreciate the solution to this problem, a brief discussion of the properties of the specimen 108 is in order. In the foregoing, it has been assumed that the specimen 108 behaves in a perfectly elastic manner, i.e., the wavenumber k is real and the wavespeed c=w/k is a constant. Even though equation (20) is derived for an elastic material, it is rigorously valid for a linear viscoelastic material provided that the damping is small. A viscoelastic material is a material which absorbs a portion of the energy which is imparted to it, or in other words, a viscoelastic material exhibits attenuation. Therefore, the wavenumber k is a complex number in that it contains a real portion and an imaginary portion, both of which become a function of frequency w. The wavenumber k is defined by:

$$k(w) = k_1(w) + ik_2(w), \text{ where } k_2/k_1 < 1. \tag{21}$$

Therefore, equation (20) may be rewritten in polar form with a magnitude M and a phase $\phi$ as:

$$e^{-i2kh} = -[H^*(w) - 1]/T_{12}T_{21} = Me^{i\phi} \tag{22}$$

or $$e^{-i2kh} = e^{2k_2h}e^{-i2k_1h}$$

Then, by equating the real and the imaginary portions, $$k_1(w) = -\phi/2h = \text{phase velocity;} \tag{23}$$
$$k_2(w) = (\ln M)/2h = \text{attenuation, and;} \tag{24}$$

$$c(w) = \frac{4\pi h}{(-\phi/f)} = w/k_1(w) = \text{wavespeed.} \tag{25}$$

Using these equations, the wavespeed of a sound wave in a material specimen and the attenuation of the specimen can be calculated using the measured transfer function, H*(w), as shown graphically by FIGS. 7-10.

Figure 7:
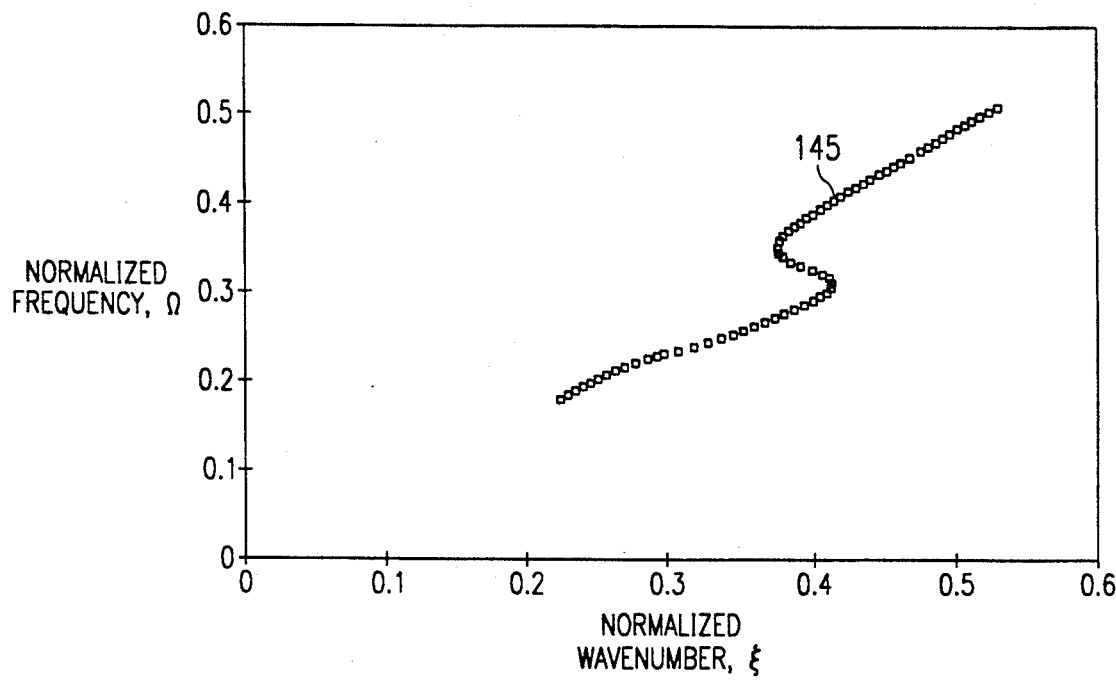
FIG. 7 illustrates a frequency response curve of phase vs. frequency.
Figure 8:
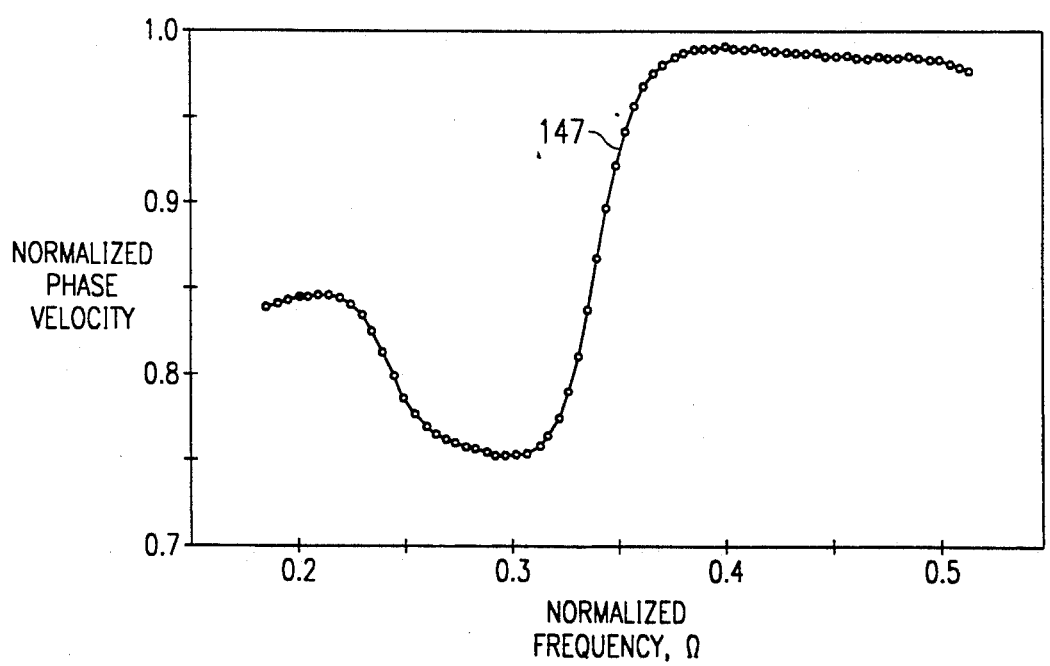
FIG. 8 illustrates a frequency response curve of normalized phase velocity vs. normalized frequency.
Figure 9:
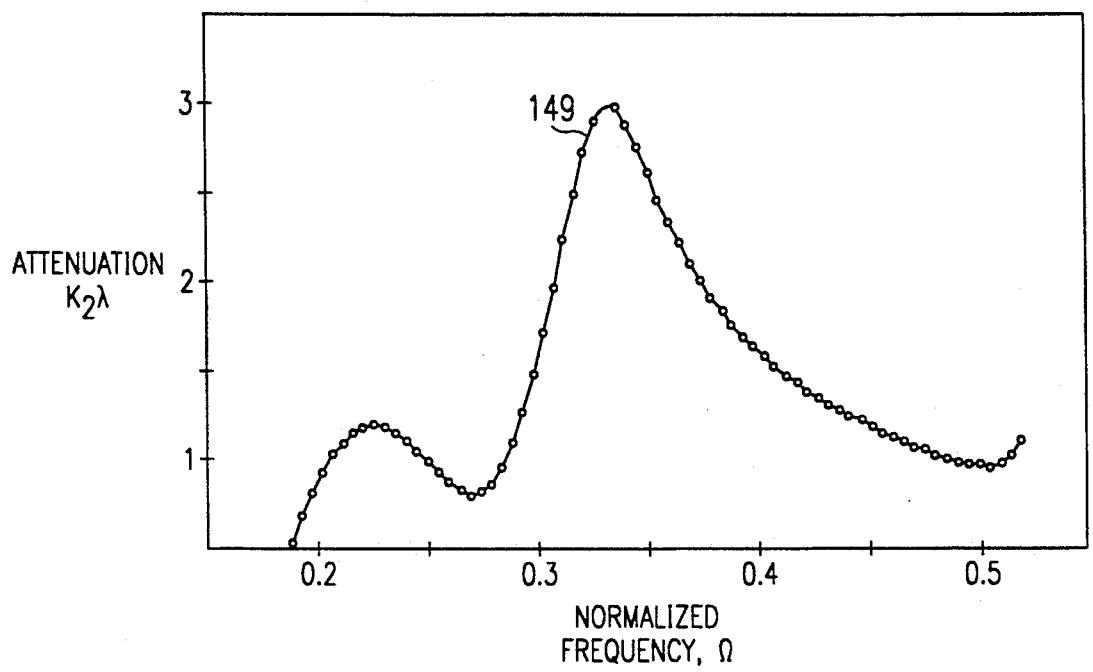
FIG. 9 illustrates a frequency response curve of normalized attenuation vs. normalized frequency.
Figure 10:
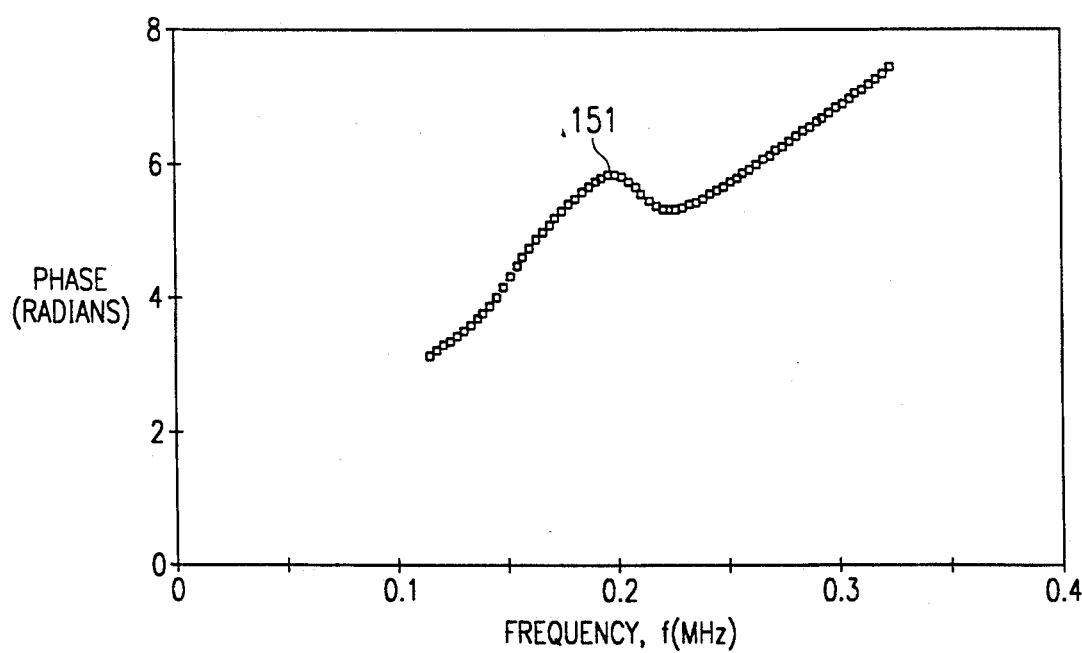
FIG. 10 illustrates a frequency response curve of phase vs. frequency.

In reference to FIGS. 7-10, the frequency-dependent nature of the specimen is advantageously utilized to determine a wide variety of parameters. This technique is equally effective for non-dispersive or dispersive material. For dispersive media, the quantity of interest is the group velocity $c_g$ which is the speed with which energy propagates in a medium. For instance, FIG. 7 shows a normalized curve 145 of the frequency w vs. wavenumber k(w). For any given frequency w, a tangent slope of the curve 145 yields the group velocity $c_g = dw/dk$ of the acoustical waves in the specimen and a secant slope of the curve 145 yields the phase velocity $c_p$ of the acoustical waves in the specimen. FIG. 8 illustrates a normalized curve 147 of the phase velocity $c_p(w)$ vs. the frequency w, so for any given frequency w, the phase velocity $c_p(w)$ can be determined. The curve 147 is determined using equation (23). FIG. 9 shows a normalized curve 149 of the attenuation $k_2(w)$ vs. the frequency w, so for any given frequency w, the attenuation $k_2(w)$ can be determined. The curve 149 is determined using equation (24). FIG. 10 illustrates a normalized curve of 151 of phase $\phi$ vs. frequency w, and is determined using equation (25). The normalized parameters are introduced to make the parameters independent of frequency for a linear viscoelastic material. For instance, the normalized wavenumber is kh and the normalized attenuation is $k_2\lambda$.

A thick specimen can be evaluated using the spacing between the zero-crossings of FIG. 5. Or, for each possible thickness of the material, a theoretical $H^*(w)$ can be computed. Then, by inserting the measured transfer function, $H^*(w)$, into the left-hand side of equation (20), the measured transfer function is equated to a theoretical $H^*(w)$ for a given material and measurement method, i.e., the right-hand side of equation (20), and the unknown parameters (k or h) of equation (20) can be determined.

B. Transmission Method

Using this technique, consider the transmitted field for the thick specimen 108. Instead of using the first reflected wave (ray 2) as a reference signal, $f(t)$, the apparatus of FIG. 3 is operated without the specimen 108 so that the acoustical wave travels solely through the medium 110. Therefore, the reference signal, $f(t)$, is equal to the incident wave:

$$f(t) = f_o(wt - k_o n) \quad (26)$$

The specimen 108 is then inserted into the elastic medium 110 between the transducers 106 and 112. Here, the signal due to the first transmitted wave (ray 4) alone is recorded. Thus, g(t) is equal to the first transmitted wave (ray 4), and as shown in equation (8):

$$g(t) = T_{12}T_{21} f_o(wt - k_o n - 2k_o a - kh). \quad (27)$$

This yields the transfer function, $H^*(w)$:

$$\frac{G^*(w)}{F^*(w)} = T_{12}T_{21} e^{-i(kh + k_0 h)}; \quad (28)$$

$$k_1(w) = -\phi/h; \quad (29)$$
$$k_2(w) = (\ln M)/h; \text{ and} \quad (30)$$

$$c = \frac{2\pi h}{(-\phi/f)}. \quad (31)$$

2. Analysis of a Thin Specimen

The previously described technique can also be used to evaluate thin specimens. As mentioned previously, a specimen is "thick" if the individual reflected or transmitted pulses can be separated in the time-domain, and a specimen is "thin" if the individual reflected or transmitted pulses cannot be separated from one another in the time-domain. As with the thick specimen, either the reflected or the transmitted waves can be used to evaluate a thin specimen.

Since the previously described reflection technique used the first two reflected waves (rays 2 and 6), and since the transmission technique used the first reflected wave (ray 2) and the first transmitted wave (ray 4), only thick specimens could be evaluated because the pulses could be separated in the time-domain, and, thus, the remaining pulses could be gated out. However, using the total reflected field as given by equation (7) or the total transmitted as given by equation (11), a thick or a thin specimen can be evaluated.

Since the frequency-dependent parameters shown in FIGS. 7-10 can be determined with only a few points on curve 144 of FIG. 5, rather than with complete cycles which form zero crossings, an extremely thin specimen on the order of 0.01 millimeters can be evaluated. It is important to remember in the following discussions that the wavenumber k is defined as in equation (21).

Figure 6:
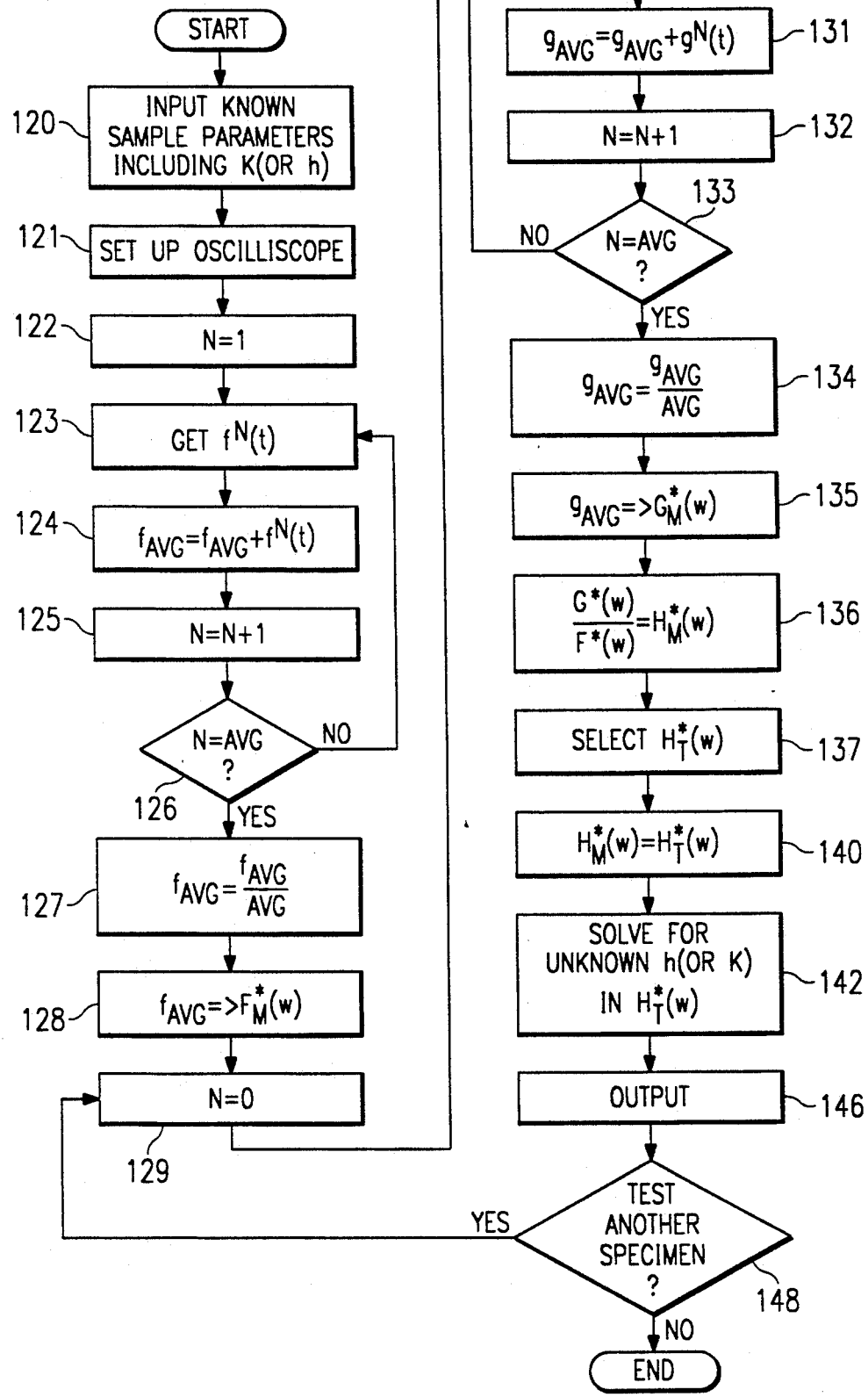
FIG. 6 illustrates a flowchart describing the computer control of the apparatus of FIG. 3.

Since the apparatus of FIG. 3 can be used to automatically evaluate thick or thin specimens, it is appropriate to discuss, in general, the role of the computer 116. Referring to FIG. 6, the computer 116 is first initialized in block 120 with the known parameters of a specimen to be tested. These may include parameters such as thickness, acoustic impedances, acoustic attenuations, and elastic moduli. Preferably, the computer 116 controls the digitizing oscilloscope 114, so the parameters of the oscilloscope 114 are initialized in block 121. These may include parameters such as sampling rate and sampling time. It is preferable to average a number of reference signals to improve the accuracy of the measurement. Therefore, N=AVG reference signals, f(t), are taken and averaged, as shown in blocks 122-127. In block 122, the counter N is initialized by setting it equal to 1. in block 123, the first reference signal f(t) is measured. In Block 124, the reference signal measured in block 123 is averaged with previously measured signals from block 123. Thus, when the first reference signal f(t) is measured in block 123 (when the counter N equals 1), $f_{avg}$ on the right-hand side of the equation in block 124 is 0. Therefore, $f_{avg}$ on the left-hand side of the equation in block 124 is the first reference signal f(t) measured in block 123. In block 125, the counter N is incremented by 1. The counter N is compared with a stored number AVG which corresponds to the number of signals f(t) to be taken and averaged. If the counter N is not equal to the number AVG in block 126, control of the program transfers back to the block 123 where another reference signal f(t) is taken. Thus, the measured reference signals f(t) from block 123 continue to be added together in block 124 until the desired number of reference signals f(t) are take as determined by the counter N equaling the stored number AVG. Once the desired number of reference signals f(t) have been taken, the reference signals are averaged in block 127 by dividing the sum $f_{avg}$ of the reference signals f(t) from the left hand of the equation in block 124 by the stored number AVG. Then, the FFT of the averaged reference signal is computed in block 128.

The procedure is essentially repeated for the specimen signal, g(t), in that g(t) is taken N=AVG times and averaged, as shown in blocks 129-134. In block 129, the counter N is initialized by setting it equal to 0. In block 130, the first specimen signal g(t) is measured. In block 131, the specimen signal measured in block 130 is averaged with previously measured signals from block 130. Thus, when the first specimen signal is measured in block 130 (when the counter N equals 0), $g_{avg}$ on the right-hand side of the equation in block 131 is 0. Therefore, $g_{avg}$ on the left-hand side of the equation in block 131 is the first specimen signal g(t) measured in block 130. In block 132, the counter N is incremented by 1. The counter N is compared with a stored number AVG which corresponds to the number of signals g(t) to be taken and averaged. If the counter N is not equal to the number AVG in block 133, control of the program transfers back to the block 130 where another specimen signal g(t) is taken. Thus, the measured specimen signals from block 130 continue to be added together in block 131 until the desired number of specimen signals g(t) are taken as determined by the counter N equaling the stored number AVG. Once the desired number of specimen signals g(t) have been taken, the specimen signals are averaged in block 134 by dividing the sum of the specimen signals g(t) from the left hand of the equation in block 131 by the stored number AVG. Then, the FFT of the averaged specimen signal is computed in block 135. The computed Fourier Transforms yield measured signals F*m(w) and G*m(w) in the frequency-domain. G*m(w) is divided by F*m(w) in block 136 to produce a measured transfer function H*m(w).

In block 137, a theoretical transfer function H*t(w) is selected, either from a memory or by choosing an appropriate subroutine. The theoretical transfer function H*t(w) is a general solution that gives the proper frequency response of the material using a particular measurement method, e.g., reflection or transmission. Therefore, the measured transfer function H*m(w) is essentially equated to the appropriate theoretical transfer function H*t(w) in block 140. Since the theoretical transfer function H*t(w) includes the unknow quantity kh, and since either k or h of the material being tested is known, the unknown quantity is determined, as shown in block 142. This quantity is then output in a proper form, graph or numeral, in block 146. Then, another specimen may be tested without taking a new reference signal, as shown in block 184. If testing another specimen is desired, control transfers to block 129 where the counter N is initialized. Then, the process of measuring the specimen signal g(t) is repeated as described above. However, if another specimen is not to be measured, the procedure ends.

A. Reflection Method

First, we will consider using the total reflected field to evaluate a thin specimen. To use the reflection method on a thin specimen, the reference signal, f(t), is determined by a separate experiment, because the first reflected wave (ray 2) cannot be measured individually due to the interference from the subsequently reflected waves. Preferably, the thin specimen is replaced by a thick specimen whose front surface is placed precisely where the front surface of the thin specimen will be during the test. Since a thick specimen is used, the first reflection from the front surface can be isolated. Therefore, f(t) is given by equation (14), and g(t) is identically equal to the entire reflected field which is given by equation (7). The Fourier Transforms of these respective signals are given below.

$$F^*(w) = R_{12}e^{-i2k_0a}F_0^*(w) \tag{32}$$

$$G^*(w) = F^*(w) + T_{12}R_{21}T_{21} \sum_{m=1}^{\infty} F_0^*(w) \cdot \tag{33}$$

$$e^{-i[2k_0a + m2kh]} \tag{34}$$

By substituting:

$$W = R_{21}^2 e^{-i2kh} \tag{35}$$

and deconvolving G*(w) and F*(w) we obtain the transfer function H*(w) as shown below.

$$\frac{G^*(w)}{F^*(w)} - 1 = \frac{T_{12}T_{21}}{R_{12}R_{21}} \sum_{m=1}^{\infty} W^m \tag{36}$$

Observing that for $|W| < 1$, $(1-W)^{-1} = 1 + W + W^2 + \ldots \infty$, and defining:

$$\beta = \frac{R_{21}R_{21}}{T_{21}T_{21}} \left( \frac{G^*(w)}{F^*(w)} - 1 \right) \tag{37}$$

then, $$W = \frac{\beta}{1 + \beta} \tag{38}$$

From W one can readily calculate the complex-valued wavenumber k(w) after having measured F*(w) and G*(w) and calculated the transfer function H*(w). Therefore, this technique is preferably implemented by the computer 116.

If a thick specimen of the particular material is unavailable, then a thick specimen of another material may be used. If the acoustic impedance $Z_0$ of the specimen material is $\rho_0 c_0$ and the acoustic impedance $Z_1$ of the other material is $\rho_1 c_1$, then the reflection coefficient R in f(t) is modified and set equal to:

$$R = (\rho_0 c_0 - \rho_1 c_1)/(\rho_0 c_0 + \rho_1 c_1) \tag{39}$$

and, therefore, $$\beta = \frac{R_{12}R_{21}}{T_{12}T_{21}} \left( \frac{G^*(w)R}{F^*(w)R_{12}} - 1 \right). \tag{40}$$

B. Transmission Method

To use the transmission method on a thin specimen, the reference signal, f(t), is determined by a separate experiment. The second transducer 112 is used as a receiver at a location x=n, where n>b. To obtain a reference signal the specimen 108 is removed from the elastic fluid 110, and the signal through fluid is recorded. Therefore, $$f(t) = u^{inc}(n,t) = f_0(wt - k_0 n). \tag{41}$$

The specimen signal, g(t), is the total transmitted field received by the transducer 112, so g(t) is obtained from equation (11):

$$g(t) = T_{12}T_{21} \sum_{m=0}^{\infty} R_{21}^{2m} f_0[wt - k_0 n - h\{(2m + 1)k - k_0\}], \tag{42}$$

The transfer function H*(w) that results from the division of the Fourier Transforms of these two signals is defined by:

$$\frac{G^*(w)}{F^*(w)} = \frac{T_{12}T_{21}e^{-ih(k-k_0)}}{1 - R_{21}^2 e^{-i2kh}} \tag{43}$$

There is one major difference between equations (38) and (43). Unlike equation (38), equation (43) is a quadratic in $W=\exp(-ikh)$. This presents some additional numerical problems which are discussed next. Equation (38) may be rewritten as $$W^2 + WY - D_0 = 0 \tag{44}$$

where $$Y = \frac{T_{12}T_{21}}{R_{21}Z_0} \frac{F^*(w)}{G^*(w)}; \tag{45}$$

$$W_0 = \exp(-ink_0); \tag{46}$$
$$D_0 = 1/R_{21}^2; \tag{47}$$

and $k_o$ is the wavenumber in water.

Therefore, this problem is solved by a simple iteration procedure. For instance, if the wavespeed c is unknown, an approximate wavespeed c is initially used in the algorithm to estimate $T_{ij}$ and $R_{ij}$. The quadratic equation (28) is solved and two roots of W are obtained. The correct root is chosen based on the fact that as the phase of W decreases, frequency increases, and for the other root the reverse is true. The resulting wavespeed c is used for the next iteration cycle, and the iteration procedure converges very rapidly (within about five iterations) to the correct value of the wavespeed c.

In the previous discussion, either the total reflected field or the total transmitted field can be analyzed to determine various parameters of the thin specimen. Since these techniques measure the frequency-dependent normalized wavenumber kh, certain parameters of the material can be calculated from the wavenumber. For example, if the thickness h of the specimen 108 is known, then the attenuation and the wavespeed can be calculated. Moreover, the elastic modulus of the specimen 108 can be calculated using:

$$E = pc^2, \tag{48}$$

where p is the density of the material. Conversely, if the elastic modulus E is known, then, tracing the previous argument backward, the wavespeed and attenuation can be calculated to determine the thickness h.

FREQUENCY-DOMAIN TECHNIQUE

In the previously discussed techniques the data was collected in the time-domain and Fourier Transforms were used to convert the data into the frequency-domain for processing. Using a variation of the previously discussed techniques, the problem can be solved directly in the frequency-domain, and an inverse Fourier Transform can be used to construct the time-domain solutions, if necessary. This revised technique takes roughly 1/10th of the time to produce a solution as the previously discussed techniques. Consequently, more difficult problems of practical interest can be solved using this technique which will be referred to as the "frequency-domain" technique.

Figure 11:
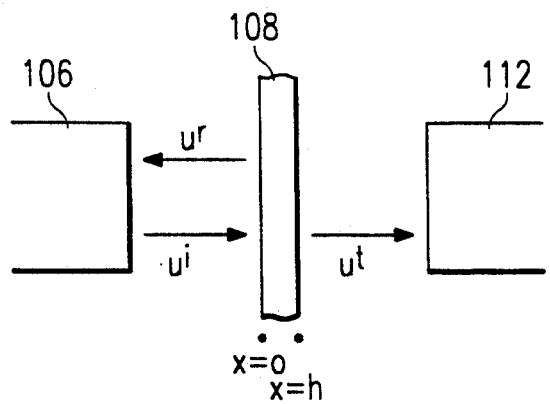
FIG. 11 illustrates a thin specimen between two transducers.

With reference to FIG. 11, the incident, reflected, and transmitted fields, $u^i$, $u^T$, and $u^t$, respectively, as shown in equations (3), (7) and (11), are redefined by:

$$u^i = A_0 e^{i(wt - k_0 x)} \tag{49}$$

$$u^r = A_r e^{i(wt + k_0 x)} \tag{50}$$

$$u^t = A_t e^{i(wt - k_0 x)} \tag{51}$$

Rewritten in this form, the standing waves within the specimen 100 are given by:

$$u^s = (Ae^{ikx} + Be^{-ikx})e^{iwt} \tag{52}$$

Notice that these waves are collected and processed in the frequency-domain with no conversion, in contrast to the time-domain technique where the collected signals were converted into the frequency-domain using a Fourier Transform. Taking equation (49) of the incident wave, for instance, the magnitude of the acoustical wave is equal to $A_0$ and the phase and the direction of the acoustical wave is given by the exponential portion of the equation. Using these representations, a thick or a thin specimen can be evaluated using either the reflected waves or the transmitted waves, as previously described. Therefore, dividing the measured reflected field by the incident wave yields a solution for the reflection measurement of this method, and dividing the measured transmitted field by the incident wave yields the solution for the transmission measurement of this method. These equations are shown below.

$$H^*(w) = \frac{A_r}{A_o} = \frac{(R^2 - 1)[1 - e^{i2kh}]}{(R + 1)^2 e^{2ikh} - (R - 1)^2}; \tag{53}$$

$$H^*(w) = \frac{A_t}{A_o} = \frac{4R\, e^{i(k+k_0)h}}{(R + 1)^2 e^{2ikh} - (R - 1)^2}; \tag{54}$$

where $$R = \frac{p^c}{p_0^c} = \frac{\text{acoustic impedance of the specimen}}{\text{acoustic impedance of water}}.$$

It is quite straightforward, but algebraically tedious, to show that equations (53) and (54) correctly reduce to equations (38) and (43), respectively.

Again, this technique, as with all of the previously mentioned techniques, can be carried out by the apparatus of FIG. 3, where the specimen 108, whether thick or thin, is placed between the two transducers 106 and 112. The fact that the specimen 108 is immersed in an elastic medium 110, such as water, presents little problem in practical applications of the above-mentioned techniques. While many companies maintain large water-immersion facilities where ultrasonic non-destructive evaluation of large specimens may be carried out, water from hoses may also be used for acoustically couping the transducers to the specimen during testing. Moreover, with a very slight change in detail to the previously mentioned techniques, the techniques can be adapted to measure in a "direct contact mode" where the transducers are in contact with or affixed to the specimen.

It should also be mentioned that the reflection or the transmission mode of measurement is used to evaluate a thick or thin specimen, depending on the practicality of such a measurement. For instance, if the fuselage of an airplane were to be evaluated, it would be impractical to fill the airplane with water in order to carry out the test in the transmission mode. It would be much more convenient to simply use the reflection mode of the test. In the following examples, various applications of the previously described methods will be shown.

Alternatively, both the transmitted field and the reflected field can be used to eliminate the first measurement in which a reference signal is collected. For instance, the total reflected field can be used as the reference signal and the total transmitted field can be used as the specimen signal, and these can be measured during the same test. The transfer function for this type of measurement using the frequency-domain technique is given below.

$$H^*(w) = \frac{A_t}{A_r} = \frac{4R \, e^{i(k+k_0)h}}{(R^2 - 1)[1 - e^{i2kh}]} \quad (55)$$

The use of both the reflected field and the transmitted field is also valid for measurements taken using the time-domain technique.

EXAMPLE 1

Thin Specimen Laminated to a Thick Specimen

Figure 12:
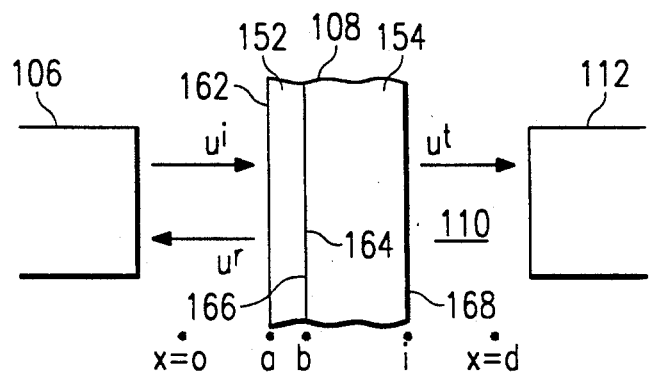
FIG. 12 illustrates a transmission measurement technique for a thin laminant on a thick subtrate.

First, the ultrasonic nondestructive evaluation of a thin specimen laminated to a thick specimen will be described in reference to FIGS. 3 and 12. The specimen 108 includes a laminant 152 of thin material, such as a ceramic coating, and a thick substrate 154, such as metal. The specimen 108 is placed in the water bath 110 between the transmitting transducer 106 and the receiving transducer 112. The specimen 108 is positioned between the transducers 106 and 112 so that the front surface 162 of the thin laminant 152 is at a position $x=a$, and, therefore, the rear surface 164 of the thin laminant 152 is positioned at $x=b$, as is the front surface 166 of the thick substrate 154. The rear surface 168 of the thick substrate 154 is positioned at $x=i$. The transducer 106 is positioned at $x=0$, and the transducer 112 is positioned at $x=d$.

The transducer 106 emits an ultrasonic acoustical wave $u^i$, which is mathematically described in equation (49). A portion $u^r$ of the incident wave is reflected back to the transducer 106, as mathematically described in equation (50). Another portion $u^t$ of the incident wave is transmitted through the specimen 108 and received by the transducer 112. The transmitted wave is mathematically described in reference to equation (51).

A. Transmission Method

First, the incident wave and the transmitted wave are used to determine the thickness of the thin laminant 152. The data corresponding to the transmitted wave is divided by the data corresponding to incident wave to produce a transfer function given below:

$$H^*(w) = A_t/A_i. \quad (56)$$

Equation (56) can be re-written as follows.

$$H^*(w) = \frac{8 Z_0 Z_1 Z_2}{(Z_0 + Z_1)(Z_1 + Z_2)(Z_2 + A_0)} \cdot$$

$$\frac{e^{-i[w(k_2 - k_0)]}}{\left[1 + \frac{(Z_2 - Z_1)(Z_1 - Z_0)}{(Z_2 - Z_1)(Z_1 - Z_0)} e^{-i2k_1h}\right]} \quad (57)$$

where $Z_0 = p_0 c_0$ (the acoustical impedance of water), $Z_1 = p_1 c_1$ (the acoustical impedance of the thin laminant 152), $Z_2 = p_2 c_2$ (the acoustical impedance of the thick substrate 154), $k_0(w) = w/c_0(w)$ (the attenuation of water), $k_1(w) = w/c_1(w)$ (the attenuation of the thin laminant 152), $k_2(w) = w/c_2(w)$ (the attenuation of the thick substrate 154), and $h$ = the thickness of the thin laminant 152.

If the transfer function $H^*(w)$ is solved for the thickness $h$, the other variables in the transfer function $H^*(w)$ should be known or measurable. For automation, the known variables are input to the computer 116. In the present example, the acoustic impedance and the attenuation of water, paint and steel are all known or measurable quantities which can easily be determined before performing a test on a particular specimen to determine the thickness of the thin laminant 152.

B. Reflection Method

Figure 13A:
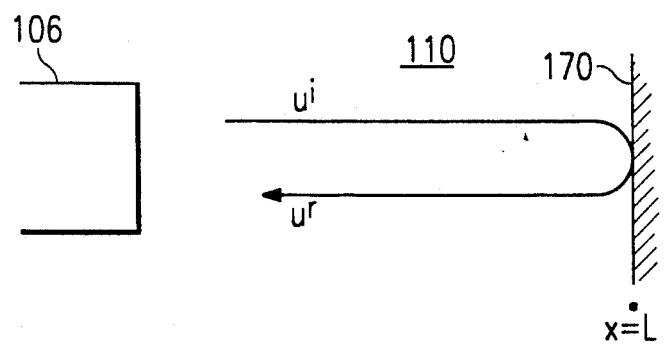
FIGS. 13a and b illustrate a reflection measurement technique for a thin laminant on a thick subtrate.
Figure 13B:
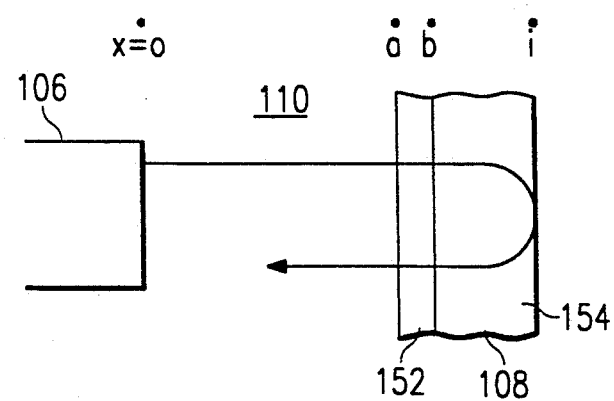

Likewise, the ultrasonic non-destructive evaluation of the specimen 108 can also be carried out in the reflection mode. Preferably, two measurements are taken, the first to determine the function $f(t)$, and the second to determine the function $g(t)$. As illustrated in FIG. 13a, the transducer 106 emits an acoustical wave which is reflected off of a block of reference material 170. The reflected wave is received by the transducer 106 and is processed as the reference signal, $f(t)$. The specimen 108 is then inserted into the water bath 110. The transducer 106 emits another acoustical wave, and the signal reflected from the back surface 168 of the thick substrate 154 is collected by the transducer 106, as shown in FIG. 13b. This signal is processed as the specimen signal, $g(t)$. Taking the Fourier Transforms of $f(t)$ and $g(t)$ and dividing $G^*(w)$ by $F^*(w)$, the transfer function $H^*(w)$ is given by:

$$H^*(w) = 16 \frac{Z_1^2}{Z_0 Z_2} \cdot \frac{Z_2 - Z_0}{Z_2 + Z_0} \cdot \frac{Z + Z_0}{Z_0 - Z} \cdot \quad (58)$$

$$\left[\frac{(Z_0 + Z_1)(Z_1 + Z_2)}{Z_0 Z_2} e^{ik_1h}\left(1 + \right.\right.$$

$$\left.\left.\frac{(Z_2 - Z_1)(Z_1 - Z_0)}{(Z_2 - Z_1)(Z_1 + Z_0)} e^{ik_1h}\right]^{-2} \cdot e^{-i2[k_0a + k_2w + k_0L]}$$

Solving for $h$ in equation (58) yields the thickness $h$ of the thin laminant 152.

While we have assumed in this example that the specimen 108 is immersed in a bath of water 110, the equations are equally valid if the water is replaced by delay rods made up of an elastic solid. The delay rods couple the specimen 108 to the transducers 106 and 112, and the only changes required in equations (57) and (58) would be to respectively replace the acoustic impedance and the acoustic attenuation of water with the acoustic impedance and acoustic attenuation of the material of which the delay rods are made.

C. Direct Contact Method

Although these techniques work very well if the specimen is coupled to the transducers 106, 112 by either an elastic liquid or delay rods, it is frequently inconvenient to use an elastic liquid or delay rods. In these situations, it is desirable to carry out the ultrasonic non-destructive evaluation of a specimen with the transducers being in direct contact with the specimen. For this example, we will assume that we wish to measure the thickness of a thin laminant on a thick substrate without immersing the specimen in water.

Figure 14A:
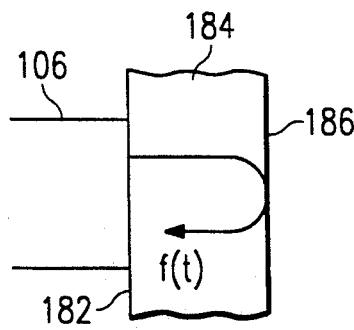
FIGS. 14a-c illustrate a direct contact measurement technique for a thin laminant on a thick substrate.

FIG. 14a illustrates the transducer 106 as being in contact with the back surface 182 of an unlaminated thick substrate 184. The transducer 106 emits a pulse which is reflected off of the front surface 186 of the thick substrate 184, and received by the transducer 106. This signal will be used as the reference signal, $f(t)$.

Figure 14B:
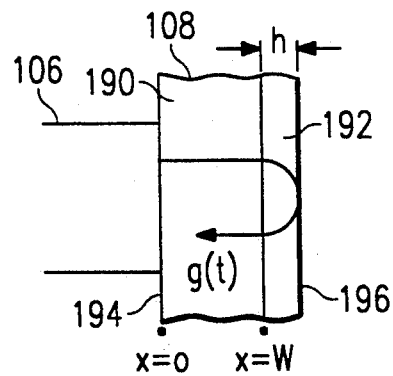

Next, a specimen 108 having a thick substrate 190 and a thin laminant 192 replaces the thick substrate 184, as shown in FIG. 14b. The rear surface 194 of the thick substrate 190 is affixed to the transducer 106. The transducer 106 emits an acoustical wave which is reflected off the front surface 196 of the thin laminant 192, and the transducer 106 receives this reflection which becomes the specimen signal, g(t). It should be noted that the thick substrate 190 has a thickness of e and the thin laminant 192 has a thickness of h.

The Fourier Transforms of $f(t)$ and $g(t)$ are taken, preferably by the apparatus shown in FIG. 3, and the transfer function $H^*(w)=G^*(w)/F^*(w)$ is determined as shown below:

$$H^*(w) = \frac{1 + \frac{(Z_2 - Z_1)}{(Z_2 + Z_1)} e^{2ik_1h}}{1 + \frac{Z_2 - Z_1}{Z_2 + Z_1} e^{-2ik_1h}} \cdot e^{-2ik_1h} \tag{59}$$

where $Z_1=p_1c_1$ (the acoustic impedance of the thin laminant), $Z_2=p_2c_2$ (the acoustic impedance of the thick substrate), and $k_1(w)=w/c_1(w)$ (the acoustic attenuation of the thin laminant).

Figure 14C:
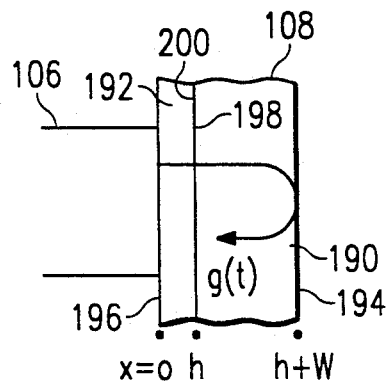

This test could also be conducted with the transducer 106 in direct contact with the front surface 196 of the thin laminant 192. In this case, the reference signal, $f(t)$, would be obtained in the same manner as described in reference to FIG. 14a. However, it will noticed in reference to FIG. 14c, that the ultrasonic wave emitted by the transducer 106 travels through the specimen 108 and reflects off of the rear surface 194 of the thick substrate 190. As shown, the rear surface 198 of the thin laminant 192 and the front surface 200 of the thick substrate 190 are located at x=h, where h is the thickness of the thin laminant 192. The rear surface 194 of the thick substrate 190 is located at x=h+q, where q is the thickness of the thick substrate 190. Taking the Fourier Transforms of $f(t)$ and $g(t)$, and dividing $G^*(w)$ by $F^*(w)$ yields the following transfer function.

$$H^*(w) = \frac{2 Z_1 e^{-ik_2h}}{(Z_1 + Z_2) e^{ik_1h} + (Z_1 - Z_2) e^{-ik_1h}} \tag{60}$$

Solving this transfer function for the variable h yields the thickness of the thin laminant 192.

EXAMPLE 2

Detection of Sub-Surface Defects

The next application to discuss concerns the detection of a sub-surface crack in a structure. A recent problem with the aging aircraft fleet of the commercial aircraft industry makes this application particularly interesting. While attempts have been made to determine the integrity of an aircraft, one of the heretofore unsolved problems has been the detection of a crack proximate the surface. This is primarily because the thickness of the structure between the surface and the crack resembles a thin specimen, and the prior art non-destructive evaluation techniques cannot resolve the signal from the crack from the signal from the surface. However, using one of the previously described methods, the sub-surface cracks and the depth of the sub-surface cracks can be detected, because the acoustical impedance and the acoustical attenuation of the aircraft structure is either known or can be measured.

Figure 15A:
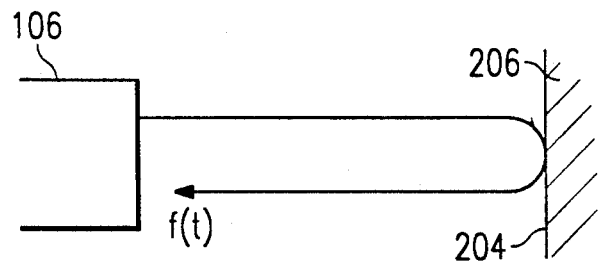
FIGS. 15a and b illustrate a reflection technique for evaluating a sub-surface crack.
Figure 15B:
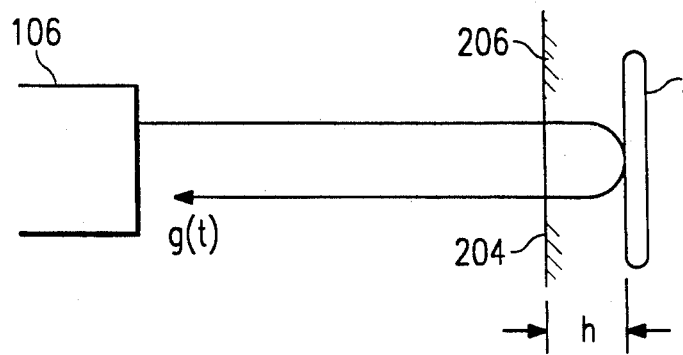

As shown is FIG. 15a, a transducer 106 is placed a predetermined distance from the surface 204 of an aircraft structure 206, and the area between the surface 204 and the transducer 106 is flooded with water. The transducer outputs an acoustical wave toward a portion of the structure 206 which does not contain a crack in order to receive a reference signal, $f(t)$. Next, the transducer 106 is moved over the surface 204 to preselected locations on the surface 204. At these preselected locations the transducer 106 emits an ultrasonic wave which is reflected from the surface or from a sub-surface crack 208 and received by the transducer 106. This signal represents the specimen signal, g(t). At a preselected location, if the transducer 106 is above a crack 208 in the structure 206, then the thickness h between the surface 204 and the crack 208 is determined.

Using the time-domain technique the Fourier Transforms of $f(t)$ and g(t) are determined, and dividing $G^*(w)$ by $F^*(w)$, the transfer function is obtained, as shown below.

$$H^*(w) = \frac{1 - \frac{(Z_2 - Z_1)}{(Z_2 + Z_1)} e^{2ikh}}{1 - \frac{(Z_2 - Z_1)}{(Z_2 + Z_1)} e^{-2ikh}} \cdot \left(-\frac{Z_2 + Z_1}{Z_2 + Z_1}\right) e^{-2ikh} \tag{61}$$

EXAMPLE 3

Evaluation of a Two Thin Laminated Plates

The next application to discuss concerns the evaluation of unknown parameters of two thin plates which are laminated together. The evaluation of each of two thin laminated plates cannot be performed in the prior art non-destructive evaluation techniques, because they cannot resolve the signal from the interface between the laminants. However, using the frequency-domain technique, each of the laminants can be evaluated, as will be seen in reference to FIGS. 16a and 16b.

Figure 16A:
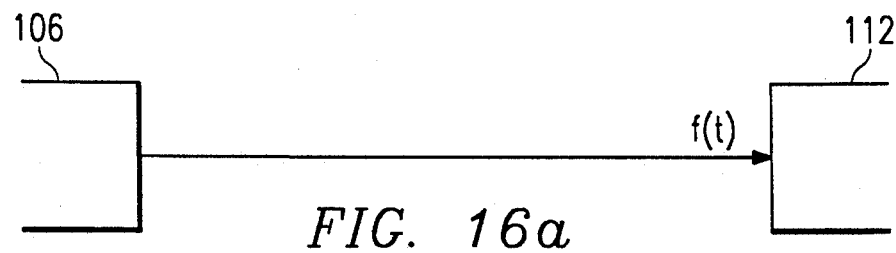
FIGS. 16a-c illustrate a reflection and a transmission technique for two thin specimens laminated together.
Figure 16B:
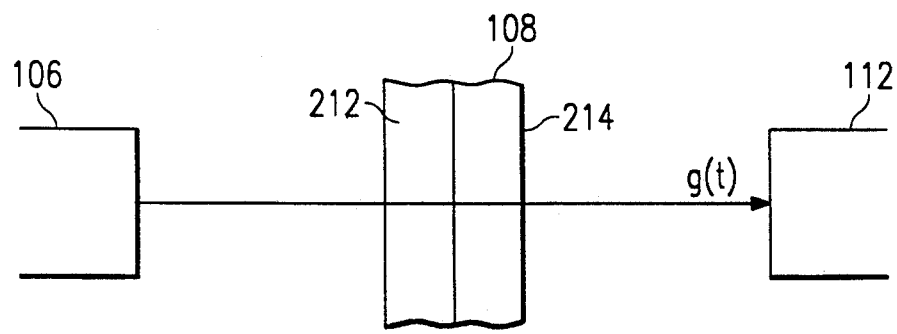

As shown is FIG. 16a, a transducer 106 is placed a predetermined distance from a transducer 112, and the area between the transducers 106,112 is flooded with water. The transducer 106 outputs an acoustical wave toward the transducer 112 in order to set a reference signal, $f(t)$. Next, a specimen 108 comprised of two thin specimens 212,214 is placed between the transducers 106,112, as shown in FIG. 16b. The transducer emits an ultrasonic signal, and the total transmitted field of the ultrasonic signal is received by the transducer 112 as g(t).

For example, let us assume that the time-domain method. By taking the Fourier Transforms of $f(t)$ and g(t), and dividing $G^*(w)$ by $F^*(w)$, the transfer function is obtained, as shown below.

$$H^*(w) = e^{ik_0h} [C e^{ik_2h} + D e^{-ik_2h}], \tag{62}$$

where C and D are constants.

Figure 16C:
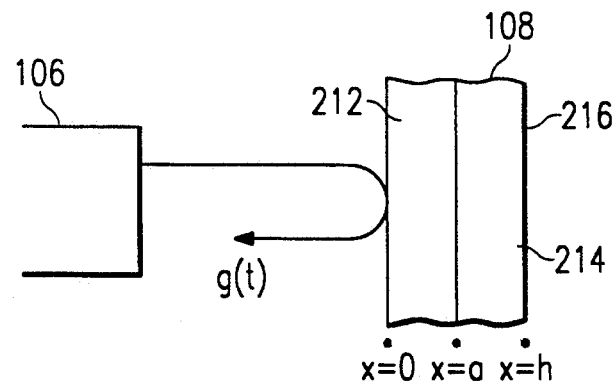

The measurement can also be taken using the reflection method. As shown in FIG. 16c, the same $f(t)$ is used, and the specimen signal g(t) is reflected off of the rear surface 216 of the laminant 214 and received by the transducer 106. This leads to the following transfer function:

$$H^*(w) + 1 = \tag{63}$$

-continued $$\frac{e^{-ik_1 a}}{Z_1} [C(Z_1 + Z_2) e^{ik_2 a} + D(Z_1 + Z_2) e^{-ik_2 a}] +$$

$$\frac{e^{+ik_1 a}}{Z_1} [C(Z_1 - Z_2) e^{ik_2 a} + D(Z_1 + Z_2) e^{-ik_2 a}]$$

where C and D are constants. In view of the techniques described above, it should be readily appreciated that the invention may be used to determine heretofore undeterminable characteristics of many types of thin specimens. While the invention is susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the appended claims.

APPENDIX A

```
10    ! THIS PROGRAM IS ENTITLED  "TR_SCAN"
20    ! THE PROGRAM DIRECTS DATA 6000 TO PERFORM FFT ON
30    !     1. WAVE TRANSMITTED WHEN NO MODEL PRESENT
40    !     2. WAVE TRANSMITTED WHEN MODEL IN THE PATH
50    ! REAL AND IMAGINARY FORMS ARE BROUGHT TO THE COMPUTER
60    ! AND WAVE SPEED AND ATTENUATION ARE CALCULATED
70    ! 1. ABOVE IS STORED AND THEN 2. IS OBTAINED TO CALCULATE AT EACH PT.
80    ! A REFERENCE NEEDED ADFTER EACH SET SO USE APPROPRIATE HOLDER
90    PRINT " THIS IS PROGRAM TR_SCAN, USE THIS FOR TRANSMISSION MODE"
100   PRINT " YOU DO NOT NEED A REFERENCE EVERY TIME "
110   PRINT " BEFORE THE NEW CYCLE YOU HAVE A CHOICE TO HAVE A NEW REF OR NOT"
120   PRINT " ****** BEST OF LUCK *******"
150   REAL Fr(520),Ph(520),Mg(520),At(520),As(3),Xs(3),V1(520)
160   DIM M$[100],V$[32000]
170   COM Sa_th,INTEGER No_pt,REAL A(520),B(520),C(520),D(520),F(520),Samp_den
180    INTEGER S,I1,I2,Circle,Location,Iteration,At_1,At_m,J,Jp
190   ! OUTPUT 715;"COUPLE=2;TRGSRC=5;TRGCPL=2;DSPM=1"&CHR$(13)
192   OUTPUT 715;"COUPLE=2;TRGSRC=5;TRGCPL=2;DSPM=1"&CHR$(13)
200   S=4096 !INPUT "INPUT NUMBER OF SAMPLING POINTS",S
210   OUTPUT 715;"NPTS="&VAL$(S)&CHR$(13)
220   P=10 ! INPUT "INPUT SAMPLING PERIOD IN nS",P
230   OUTPUT 715;"PERIOD="&VAL$(P)&"nS"&CHR$(13)
240   Del_ay=95 ! INPUT "INPUT DELAY YOU WANT TO SET IN uS",Del_ay
250   OUTPUT 715;"DELAY="&VAL$(Del_ay)&"uS"&CHR$(13)
260   W=64 ! INPUT "INPUT THE NUMBER OF WAVES YOU WANT TO AVERAGE",W
270   OUTPUT 715;"AVGCNT="&VAL$(W)&CHR$(13)
280   OUTPUT 715;"LINLEN=32000;FLDLEN=127"&CHR$(13)
290   OUTPUT 715;"XSCL=1;X;KEY=1038"&CHR$(13)
300   Sa_th=.3302   !INPUT "INPUT SAMPLE THICKNESS IN mm ",Sa_th
310   R1=.8
320   Rm=1.4
330   Inp_speed=6.2
340   Samp_den=2.695
350   R$=VAL$(2)
360   GOTO 410
370   INPUT "INPUT RANGE OF FREQUENCY FOR CALCULATIONS",R1,Rm
380   INPUT "INPUT SAMPLE WAVESPEED IN mm/usec; NEED NOT BE PRECISE",Inp_speed
390   INPUT "INPUT DENSITY OF SAMPLE IN gr/c.c.; BE PRECISE",Samp_den
400   INPUT "DO YOU WANT PRINT OUT ON PRINTER-1 OR SCREEN-2",R$
410   IF R$=CHR$(49) THEN ASSIGN @P1 TO 701
420   IF R$=CHR$(50) THEN ASSIGN @P1 TO 1
430   OUTPUT 1;"DATE   ";DATE$(TIMEDATE)
440   OUTPUT 1;"TIME   ";TIME$(TIMEDATE)
450   GOTO 550
```

```
460  INPUT "INPUT SAMPLE NUMBER",Samp_num$
470  INPUT "INPUT LOAD STEP",Load_st$
480  INPUT "TRANSDUCER FERQUENCY",Tr_freq$
490  INPUT "INPUT TEMPERATURE",Temp
500  OUTPUT @P1;"    Sample Number        =";Samp_num$
510  OUTPUT @P1;"    Sample Thickness     =";Sa_th
520  OUTPUT @P1;"    Load Step            =";Load_st$
530  OUTPUT @P1;"    Transducer Frequency =";Tr_freq$
540  OUTPUT @P1;"    Test temperature     =";Temp
550  LOCAL 715
560  Sig_len=S*P*1.E-9
570  I1=INT(Sig_len*R1*1.E+6)+1    ! * FIRST POINT IN THE RANGE *
580  I2=INT(Sig_len*Rm*1.E+6)      ! * LAST POINT IN THE RANGE *
590  No_pt=I2-I1+1                 ! * TOTAL NUMBER OF POINTS *
600  T0=2.*PI*Sa_th/1.479          ! * t0 FOR WATER *
610  FOR I=1 TO No_pt
620  Freq=(I1+I-1)/Sig_len         ! * FREQUENCY AT EACH POINT OF CALCULATION *
630  Sx=Sx+Freq                    ! ! SUM OF FREQ AND THEIR SQUARES FOR USE
640  Sxx=Sxx+Freq*Freq             ! ! IN LEAST SQUARES FIT LATER *
650  Fr(I)=Freq
660  NEXT I
670  At_i=INT(No_pt/2.-10)         .! !TAKING ONLY TWENTYONE POINTS
680  At_m=INT(No_pt/2.+10)         ! ! FOR ATTENUATION CALCULATIONS
690  IF At_i<2 THEN At_i=2         ! ! FROM THE CENTRAL FREQUENCY
700  IF At_m>No_pt THEN At_m=No_pt ! ! TEN ON EACH SIDE
710  GOTO 780
720  ASSIGN @P1 TO "CP"
730  ENTER @P1;No_pt
740  FOR I=1 TO No_pt
750  ENTER @P1;A(I),B(I),C(I),D(I)
760  NEXT I
770  GOTO 1430
780  ! *********** INITIAL SETTINGS AND CALCULATIONS OVER *****************
790  ! ------------------------------------------------------------------
800  Location=1
810  Circle=1
820  OUTPUT 715;"TRCSRC=BUF.A1"&CHR$(13)
830  IF Circle=1 THEN
840      INPUT "SET REFERENCE SIGNAL WITH NO SAMPLE,PRESS RETURN WHEN READY",R$
850      MAT A= (0.)
860      MAT B= (0.)
870  END IF
880  IF Circle=2 THEN
890      INPUT "MOVE TO THE LOCATION AND PRESS RETURN WHEN READY",R$
900      MAT C= (0.)
910      MAT D= (0.)
920  END IF
930  OUTPUT 715;"PROC;AVGCLR;AVGM=2"&CHR$(13)
940  C1=0
950  OUTPUT 715;"CURAVG"&CHR$(13)
960  ENTER 715;Cur$
970  C2=C1+1
980  C1=VAL(Cur$)
990  IF C2=W THEN
1000             OUTPUT 715;"AVGM=3"&CHR$(13)
1010             GOTO 1050
```

```
1020 ELSE
1030       GOTO 950
1040 END IF
1050 OUTPUT 715;"TRCSRC=AVG.A1"&CHR$(13)
1060 OUTPUT 715;"REAL=FFT(AVG.A1,,0,0,0,17)"&CHR$(13)
1070 IF S<=1024 THEN
1080                   GOTO 1130
1090 ELSE
1100     IF S=2048 THEN WAIT 5
1110     IF S=4096 THEN WAIT 10
1120 END IF
1130 Round=1                    ! * ROUND 1 TO GET REAL PART OF FFT *
1140 J=1                        ! * ROUND 2 TO GET IMAG PART OF FFT *
1150 IF Round=1 THEN M$="REAL("&VAL$(I1)&","&VAL$(I2)&")"&CHR$(13)
1160 IF Round=2 THEN M$="IMAG("&VAL$(I1)&","&VAL$(I2)&")"&CHR$(13)
1170 OUTPUT 715;M$
1180 ENTER 715;V$
1190 Str_len=LEN(V$)
1200 N=POS(V$,",")          ! * LOCATE POSITION OF , IN THE STRING *
1210 N2=N-1
1220 IF N=0 THEN N2=Str_len
1230 Sm_str$=V$[1,N2]           ! * REMOVE THE FIRST VALUE FROM THE STRING *
1240 IF Circle=1 THEN
1250            IF Round=1 THEN A(J)=VAL(Sm_str$) ! * REAL IN REFERENCE SIGNAL *
1260            IF Round=2 THEN B(J)=VAL(Sm_str$) ! * IMAG IN REFERENCE SIGNAL *
1270 ELSE
1280            IF Round=1 THEN C(J)=VAL(Sm_str$)   ! * REAL IN TOTAL SIGNAL *
1290            IF Round=2 THEN D(J)=VAL(Sm_str$)   ! * IMAG IN TOTAL SIGNAL *
1300 END IF
1310 J=J+1
1320 IF N=0 THEN GOTO 1350
1330 V$=V$[N+1,Str_len]
1340 GOTO 1190
1350 IF Round=1 THEN
1360                 Round=2
1370                 GOTO 1140
1380 END IF
1390 IF Circle=1 THEN
1400      Circle=2
1410      GOTO 820
1420 END IF
1430 ! ****************** DATA COLLECTION OVER ******************************
1440 ! -----------------------------------------------------------
1450 Samp_speed=Inp_speed
1460 Iteration=1
1470 K=0     ! * KEEPS TRACK OF # OF 2*PI CIRCLES MADE IN MOD 0-INF *
1480 MAT Ms= (0.)
1490 MAT Ph= (0.)
1500  CALL Refl_trans(Samp_speed,Samp_den,T12,T21,R21)
1510  Con0=1./(R21*R21)
1520  Con3=T12*T21*Con0
1530 FOR I=1 TO No_pt
1540 F1=A(I)
1550 F2=B(I)
1560 G1=C(I)
1570 G2=D(I)
```

```
1580 Den=G1*G1+G2*G2
1590 ! NOW CALCULATE THE DELAY MEDIUM PROPERTIES
1600 R0=(G1*F1+G2*F2)/Den
1610 I0=(F2*G1-F1*G2)/Den
1620 T=T0*Fr(I)/1.E+6
1630 T1=T/(2.*PI)
1640 T=(T1-INT(T1))*2.*PI    !* T CONVERTED MODULO 2*PI)
1650 Y1=Con3*(R0*COS(T)-I0*SIN(T))
1660 Y2=Con3*(R0*SIN(T)+I0*COS(T))
1670 Aa=Y1*Y1-Y2*Y2+4.*Con0
1680 Bb=2.*Y1*Y2
1690 X2=SQR((SQR(Aa*Aa+Bb*Bb)-Aa)/2)
1700 X1=Bb/(2.*X2)                     !* SOLVING QUADRATIC EQUATION *
1710 Real1=(-Y1-X1)/2.
1720 Imag1=-(-Y2-X2)/2.                !* FIRST ROOTS *
1730 Real2=(-Y1+X1)/2.
1740 Imag2=-(-Y2+X2)/2.                !* SECOND ROOTS *
1750 Phase1=ATN(Imag1/Real1)           !* PHASE FROM FIRST ROOT *
1760 Mag1=SQR(Real1^2+Imag1^2)         !* MAGNITUDE FROM FIRST ROOT *
1770 Phase2=ATN(Imag2/Real2)           !* PHASE FROM SECOND ROOT *
1780 Mag2=SQR(Real2^2+Imag2^2)         !* MAGNITUDE FROM SECOND ROOT *
1790 ! ****** FIX PROPER Quadrants FOR PHASE *******
1800 IF Real1>0 THEN
1810              Q1=1
1820              IF Imag1<0 THEN Q1=4
1830 END IF
1840 IF Real1<0 THEN
1850              Q1=2
1860              IF Imag1<0 THEN Q1=3
1870  END IF
1880  IF Q1=1 THEN GOTO 1940
1890  IF Q1=4 THEN
1900              Phase1=Phase1+2.*PI
1910              GOTO 1940
1920  END IF
1930  Phase1=Phase1+PI
1940  IF Real2>0 THEN
1950              Q2=1
1960              IF Imag2<0 THEN Q2=4
1970  END IF
1980  IF Real2<0 THEN
1990              Q2=2
2000              IF Imag2<0 THEN Q2=3
2010  END IF
2020  IF Q2=1 THEN GOTO 2080
2030  IF Q2=4 THEN
2040              Phase2=Phase2+2.*PI
2050              GOTO 2080
2060  END IF
2070  Phase2=Phase2+PI
2080  !****** THE SELECTION FOR THE CORRECT ROOT STARTS NOW *****
2090  IF I=1 THEN
2100      IF Mag1<Mag2 THEN
2110          Mag=Mag1
2120          Phase=Phase1
```

```
2130        L=1
2140        Q=Q1
2150      ELSE
2160        Mag=Mag2
2170        Phase=Phase2
2180        L=2
2190        Q=Q2
2200      END IF
2210      GOTO 2590
2220    END IF
2230 D1=Phase-Phase1
2240 D2=Phase-Phase2
2250 IF L=2 THEN GOTO 2330
2260 IF D1>0 THEN
2270    IF D2>0 THEN GOTO 2310
2280 END IF
2290 IF D1>0 THEN GOTO 2390
2300 IF D2>0 THEN GOTO 2480
2310 IF D1<D2 THEN GOTO 2390
2320 GOTO 2480
2330 IF D1>0 THEN
2340    IF D2>0 THEN GOTO 2380
2350 END IF
2360 IF D2>0 THEN GOTO 2480
2370 IF D1>0 THEN GOTO 2390
2380 IF D2<D1 THEN GOTO 2480
2390 IF Mag2>1 THEN
2400    IF Mag1<1 THEN GOTO 2520
2410    IF Mag1<Mag2 THEN GOTO 2520
2420 END IF
2430 Phase=Phase2
2440 Mag=Mag2
2450 L=2
2460 Q=Q2
2470 GOTO 2560
2480 IF Mag1>1 THEN
2490    IF Mag2<1 THEN GOTO 2430
2500    IF Mag2<Mag1 THEN GOTO 2430
2510 END IF
2520 Phase=Phase1
2530 Mag=Mag1
2540 L=1
2550 Q=Q1
2560 IF Q3=4 THEN
2570           IF Q=1 THEN K=K+1
2580 END IF
2590 P=Phase+K*2.*PI
2600 Ph(I)=P          !* STORING SLOPE IN PH(J) *
2610 Mg(I)=Mag        !* STORE MAGNITUDE IN MG(J) *
2620 Q3=Q
2630 NEXT I
2640 Sy=0.       ! * SUM OF Ph(I) *
2650 Sxy=0.      ! * SUM OF Fr(I)*Ph(I) *
2660 FOR I=1 TO No_pt
2670 Sy=Sy+Ph(I)
2680 Sxy=Sxy+Fr(I)*Ph(I)
```

```
2690 F(I)=Fr(I)/1.E+6
2700 NEXT I
2710 Slope=(Sxy-Sx*Sy/No_pt)/(Sxx-Sx*Sx/No_pt)
2720 Intc=(Sy*Sxx-Sxy*Sx)/(No_pt*Sxx-Sx*Sx)
2730 Wave_speed=2.*PI*Sa_th/(Slope*1.E+6)
2740 Er=ABS(Samp_speed-Wave_speed)*100./Wave_speed
2750 IF Er<.01 THEN GOTO 2800
2760 Samp_speed=Wave_speed
2770 Iteration=Iteration+1
2780 IF Iteration=10 THEN GOTO 2800
2790 GOTO 1470
2800 PRINT "WAVE SPEED =";Wave_speed;"mm/usec after Iterations=";Iteration
2810 FOR I=1 TO No_pt
2820 St_er=St_er+(Ph(I)-Slope*Fr(I)-Intc)^2
2830 NEXT I
2840 St_error=SQR(St_er/(No_pt-1))
2850 PRINT "WITH STANDARD ERROR=",St_error
2860 ! --------------------------------------------------------
2870 ! NOW SEARCH FOR THE CORRECT WAVESPEED WHICH WILL MINIMIZE LSE
2880 Jm=30
2890 D1=Wave_speed-(1./(1/Wave_speed+1./(4.*PI*Sa_th*R1)))
2900 Spd=Wave_speed-D1
2910 Scl=D1/15
2920 FOR J=1 TO Jm
2930 Sp=Spd+(J-1)*Scl
2940 CALL Lser(Sp,Lse,An,Bn)
2950 ! PRINT "SP,LSE=",Sp,Lse
2960 IF J=1 THEN
2970    As(1)=Lse
2980    As(2)=Lse
2990    As(3)=Lse
3000 END IF
3010 IF Lse>As(3) THEN
3020    Xs(1)=Sp-2.*Scl
3030    Xs(2)=Sp-Scl
3040    Xs(3)=Sp
3050    A3=As(3)
3060    A2=As(2)
3070    As(3)=Lse
3080    As(2)=A3
3090    As(1)=A2
3100    CALL Newt(As(*),Xs(*),Sp_min)
3110    Sp=Sp_min
3120    GOTO 3270
3130 END IF
3140 IF Lse<As(3) THEN
3150    IF J=Jm THEN
3160       PRINT "NO MINIMA FOUND FOR WAVESPEED"
3170       GOTO 3760
3180    END IF
3190    A1=As(1)
3200    A2=As(2)
3210    A3=As(3)
3220    As(3)=Lse
3230    As(2)=A3
3240    As(1)=A2
```

```
3250    END IF
3260    NEXT J
3270    CALL Lser(Sp,Lse,An,Bn)
3280    CALL Refl_trans(Sp,Samp_den,T12,T21,R21)
3290    Va=.01
3300    Jm=20
3310    FOR J=1 TO Jm
3320    K=-Va*J
3330    C1=2.*Sa_th*K/Sp
3340    Sum_dif=0.
3350    FOR I=1 TO No_pt
3360    X=R21*R21*EXP(C1*F(I))
3370    Vr=.5*(X+1/X)
3380    V1(I)=An*F(I)+Bn
3390    Sum_dif=Sum_dif+(V1(I)-Vr)^2
3400    NEXT I
3410    !PRINT "CHECK FOR ATTENUATION"
3420    ! PRINT K,Sum_dif
3430    IF J=1 THEN
3440        As(1)=Sum_dif
3450        As(2)=Sum_dif
3460        As(3)=Sum_dif
3470    END IF
3480    IF Sum_dif>As(3) THEN
3490        Xs(1)=K+2.*Va
3500        Xs(2)=K+Va
3510        Xs(3)=K
3520        A3=As(3)
3530        A2=As(2)
3540        As(3)=Sum_dif
3550        As(2)=A3
3560        As(1)=A2
3570        IF As(1)=As(2) OR As(2)=As(3) THEN
3580            Va=Va/2
3590            GOTO 3300
3600        END IF
3610        CALL Newt(As(*),Xs(*),Kmin)
3620        GOTO 3760
3630    END IF
3640    IF Sum_dif<As(3) THEN
3650        IF J=Jm THEN
3660            PRINT "NO MINIMA FOUND FOR ATTENUATION"
3670            GOTO 3760
3680        END IF
3690        A2=As(2)
3700        A3=As(3)
3710        As(3)=Sum_dif
3720        As(2)=A3
3730        As(1)=A2
3740    END IF
3750    NEXT J
3760    PRINT "SP_MIN=",Sp_min
3770    PRINT "KMIN=",Kmin
3780    BEEP 240,.5
3790    INPUT "DO YOU WANT TO PRINT THIS DATA",Res$
3800    IF Res$=CHR$(78) THEN GOTO 3850
```

```
3810 PRINTER IS 701
3820 PRINT USING '''WAVE SPEED='',2D.4D,'' mm/uSec''';Sp_min
3830 PRINT USING '''ATTENUATION='',2D.6D,'' Nepers''';Kmin
3840 PRINTER IS 1
3850 INPUT 'DO YOU WANT TO CARRY ON',Res$
3860 IF Res$=CHR$(78) THEN GOTO 3900
3870 INPUT 'DO YOU WANT TO GET A NEW REFERENCE ? Y/N',Res$
3880 IF Res$=CHR$(78) THEN GOTO 820
3890 GOTO 810
3900 END
3910 !*************************************************************
3920 !******* SUBROUTINE REFL_TRANS (REFL TRANS COEFF CALCULATION)***********
3930 SUB Refl_trans(Samp_speed,Samp_den,T12,T21,R21)
3940 Sp_rat=1.485/Samp_speed
3950 Den_rat=.998/Samp_den
3960 Zee=Sp_rat*Den_rat
3970 T12=2.*Zee/(1+Zee)
3980 T21=2./(1+Zee)
3990 R12=(Zee-1)/(Zee+1)
4000 R21=-R12
4010 SUBEND
4020 !*************************************************************
4030 !*************** SUBROUTINE LSER (LEAST ERROR CALCULATION)************
4040 SUB Lser(Sp,Lse,An,Bn)
4050 COM Sa_th,INTEGER No_pt,REAL A(*),B(*),C(*),D(*),F(*),Samp_den
4060 CALL Refl_trans(Sp,Samp_den,T12,T21,R21)
4070 DIM V1(520)
4080 Sum_fr=0
4090 Sum_fr2=0
4100 Sum_v1=0
4110 Sum_frv1=0
4120 FOR I=1 TO No_pt
4130 Mfx=SQR(A(I)*A(I)+B(I)*B(I))
4140 Msx=SQR(C(I)*C(I)+D(I)*D(I))
4150 P=Mfx/Msx
4160 T1=COS(4.*PI*Sa_th*F(I)/Sp)
4170 T2=.5*(T12*T21*P/R21)^2
4180 V1(I)=T1+T2
4190 Sum_fr=Sum_fr+F(I)
4200 Sum_fr2=Sum_fr2+F(I)*F(I)
4210 Sum_v1=Sum_v1+V1(I)
4220 Sum_frv1=Sum_frv1+F(I)*V1(I)
4230 NEXT I
4240 Dn=No_pt*Sum_fr2-(Sum_fr)^2
4250 An=(No_pt*Sum_frv1-Sum_fr*Sum_v1)/Dn
4260 Bn=(Sum_fr2*Sum_v1-Sum_fr*Sum_frv1)/Dn
4270 Lse=0
4280 FOR I=1 TO No_pt
4290 Lse=Lse+(An*F(I)+Bn-V1(I))^2
4300 NEXT I
4310 SUBEND
4320 !*************************************************************
4330 !********** SUBROUTINE NEWT *************************************
4340 ! THIS SUBROUTINE CALCULATES NEWTONS INTERPOLATION POLYNOMIAL ******
4350 SUB Newt(A(*),X(*),Val_ret)
4360 FOR J=1 TO 2
```

```
4370 FOR I=3 TO J+1 STEP -1
4380 A(I)=(A(I)-A(I-1))/(X(I)-X(I-J))
4390 NEXT I
4400 NEXT J
4410 Val_ret=(A(3)*(X(1)+X(2))-A(2))/(2.*A(3))
4420 SUBEND
```

I claim:

1. A method for non-destructively evaluating a material, comprising the steps of:
   transmitting an ultrasonic wave having a frequency within a predetermined frequency range into said material;
   receiving said ultrasonic wave from said material;
   measuring a frequency response of said material at frequencies within said predetermined frequency range from said received ultrasonic wave; and
   determining a frequency-dependent normalized wavenumber in said material from said frequency response.

2. The method, as set forth in claim 1, wherein said wavenumber is a complex mathematical quantity having a real portion and an imaginary portion.

3. The method, as set forth in claim 2, wherein said real portion is correlative to a speed of said ultrasonic wave within said material.

4. The method, as set forth in claim 3, wherein the speed of said ultrasonic wave in said material is dependent upon the frequency of said ultrasonic wave.

5. The method, as set forth in claim 2, wherein said imaginary portion is correlative to an amount of attenuation of said ultrasonic wave produced by said material.

6. The method, as set forth in claim 5, wherein the attenuation of said ultrasonic wave in said material is dependent upon the frequency of said ultrasonic wave.

7. A method for non-destructively evaluating a material, comprising the steps of:
   transmitting an ultrasonic wave having a frequency within a preselected frequency range into said material;
   receiving said ultrasonic wave from said material;
   measuring a frequency response of said material at frequencies within said preselected frequency range from said received ultrasonic wave; and
   equating said measured frequency response to a preselected frequency-dependent function of said material to determine an unknown parameter of said material.

8. The method, as set forth in claim 7, wherein said step of measuring comprises:
   calculating the Fourier Transform of said received ultrasonic wave; and
   dividing the Fourier Transform of said received ultrasonic wave by a predetermined frequency response to yield the frequency response of said material.

9. The method, as set forth in claim 7, wherein said step of equating comprises:
   calculating said frequency-dependent function of said material using a predetermined number of known parameters of said material, said frequency-dependent function having an unknown variable which is correlative to said unknown parameter of said material;
   equating said frequency-dependent function to said measured frequency response; and
   calculating said unknown variable.

10. An apparatus for evaluating a specimen, comprising:
    a generator being adapted to deliver an electrical pulse having a predetermined duration;
    a transducer being adapted to receive said electrical pulse, convert said electrical pulse into an ultrasonic acoustical wave correlative thereto, direct said ultrasonic acoustical wave toward said specimen, detect ultrasonic acoustical waves reflected from said specimen, and convert said reflected acoustical waves into an electronic signal correlative thereto;
    a computer being adapted to receive said electronic signal, determine a frequency response of said specimen in response to said electronic signal, and determine a frequency-dependent wavenumber in said specimen from said frequency response.

11. The apparatus, as set forth in claim 10, wherein said computer:
    stores a predetermined number of known parameters of said specimen, said known parameters being known variables in a given equation and said wavenumber being an unknown variable; and
    uses said equation to calculate said wavenumber from the determined frequency response of said specimen.

12. An apparatus for evaluating a material, comprising:
    a generator being adapted to deliver an electrical pulse having a predetermined duration;
    a transducer being operably connected to said generator to receive said electrical pulse, said transducer converting said electrical pulse into an ultrasonic acoustical wave correlative to said electrical pulse;
    said transducer being positioned to direct said ultrasonic acoustical wave toward said material and to detect ultrasonic acoustical waves reflected from said material, and said transducer converting said reflected acoustical waves into an electronic signal correlative to said reflected acoustical waves; and
    a computer being operably connected to said transducer to receive said electronic signal, said computer being programmed to determine a frequency response of said material in response to said electronic signal, and to determine a frequency-dependent normalized wavenumber in said material from said frequency response.

13. A method for evaluating a material having a known thickness, comprising the steps of:
    imparting an ultrasonic wave into said material;
    receiving the ultrasonic wave from said material;
    determining the frequency response of said material within a predetermined frequency range from said received ultrasonic wave;
    calculating the attenuation of said material for ultrasonic waves having a frequency within said predetermined frequency range; and
    calculating the speed with which ultrasonic waves having a frequency within said predetermined frequency range propagate through said material.

14. A method for evaluating a material having a known attenuation and through which speed of an ultrasonic wave is known, comprising the steps of:
- imparting an ultrasonic wave into said material;
- receiving the ultrasonic wave from said material;
- determining the frequency response of said material within a predetermined frequency range from said received ultrasonic wave; and
- calculating the thickness of said material in response to said determined frequency response.

15. The method, as set forth in claim 14, wherein said step of determining comprises:
- calculating the Fourier Transform of said received ultrasonic wave; and
- dividing the Fourier Transform of said received ultrasonic wave by a predetermined frequency response to yield the frequency response of said material.

16. The method, as set forth in claim 14, wherein said step of calculating comprises:
- relating an unknown thickness to an equation determined by said known speed and said known attenuation, said equation having the frequency response of said material as an unknown variable; and
- replacing said unknown variable with the frequency response of said material; and
- solving said equation for said unknown thickness.

17. A method for non-destructively evaluating a material using at least one transducer being adapted to emit ultrasonic waves, comprising the steps of:
- determining the frequency response of said transducer;
- transmitting an ultrasonic wave having a frequency within a predetermined frequency range into said material;
- receiving said ultrasonic wave from said material;
- determining the frequency response of said received ultrasonic wave;
- dividing the frequency response of said received ultrasonic wave by the frequency response of said transducer, said division producing the frequency response of said material; and
- determining phase and magnitude of the frequency response of said material, phase velocity of said ultrasonic wave within said material being correlative to the phase and attenuation of said material being correlative to the magnitude.

18. A method for non-destructively evaluating a thin material, comprising the steps of:
- delivering a first ultrasonic signal from a first transducer;
- receiving said first ultrasonic signal by a second transducer;
- calculating the Fourier Transform of said received first ultrasonic signal;
- acoustically coupling said thin material between said first transducer and said second transducer;
- delivering a second ultrasonic signal from said first transducer to said thin material;
- receiving a portion of said second ultrasonic signal transmitted through said thin material by said second transducer;
- calculating the Fourier Transform of said received portion;
- dividing the Fourier Transform of said received portion by the Fourier Transform of said received first ultrasonic signal, said division producing a measured transfer function;
- equating said measured transfer function to a preselected transfer function corresponding to said thin material, said preselected transfer function having at least one unknown variable, said unknown variable being related to said thin material; and
- solving for said unknown variable.

19. A method for non-destructively determining the unknown thickness of a thin material, comprising the steps of:
- delivering a first ultrasonic signal from a first transducer;
- receiving said first ultrasonic signal by a second transducer;
- calculating the Fourier Transform of said received first ultrasonic signal;
- acoustically coupling said thin material between said first transducer and said second transducer;
- delivering a second ultrasonic signal from said first transducer to said thin material;
- receiving a portion of said second ultrasonic signal transmitted through said thin material by said second transducer;
- calculating the Fourier Transform of said received portion;
- dividing the Fourier Transform of said received portion by the Fourier Transform of said received first ultrasonic signal, said division producing a measured transfer function;
- equating said measured transfer function to a preselected transfer function corresponding to said thin material, said preselected transfer function including the unknown thickness of said thin material; and
- solving said equation for the unknown thickness.

20. A method for non-destructively determining speed and attenuation of an ultrasonic wave in a material of known thickness, comprising the steps of:
- delivering a first ultrasonic wave from a first transducer;
- receiving said first ultrasonic wave by a second transducer;
- calculating the Fourier Transform of said received first ultrasonic wave;
- acoustically coupling said material between said first transducer and said second transducer;
- delivering a second ultrasonic wave from said first transducer to said material;
- receiving a portion of said second ultrasonic wave transmitted through said material by said second transducer;
- calculating the Fourier Transform of said received portion;
- dividing the Fourier Transform of said received portion by the Fourier Transform of said received first ultrasonic wave, said division producing a measured transfer function; and
- determining phase and magnitude of said measured transfer function, the speed of said ultrasonic wave within said material being correlative to the phase and the attenuation of said material being correlative to the magnitude.

21. A method for non-destructively evaluating a thin material, comprising the steps of:
- acoustically coupling an ultrasonic transducer to a reference material;
- delivering a first ultrasonic signal from said transducer to said reference material, said transducer receiving a portion of said first ultrasonic signal reflected from said reference material;

calculating the Fourier Transform of said received first ultrasonic signal;

acoustically coupling said thin material to said transducer;

delivering a second ultrasonic signal from said transducer to said thin material;

receiving a portion of said second ultrasonic signal reflected from said thin material by said transducer;

calculating the Fourier Transform of said received second ultrasonic signal;

dividing the Fourier Transform of said received second ultrasonic signal by the Fourier Transform of said received first ultrasonic signal, said division producing a measured transfer function;

equating said measured transfer function to a preselected transfer function having known parameters of said thin material, said preselected transfer function having at least one unknown parameter, said unknown parameter being related to said thin material; and solving for said unknown parameter.

* * * * *